(12) United States Patent
Umemoto

(10) Patent No.: US 7,534,509 B2
(45) Date of Patent: May 19, 2009

(54) AMBIENT-TEMPERATURE MOLTEN SALTS AND PROCESS FOR PRODUCING THE SAME

(75) Inventor: Teruo Umemoto, Denver, CO (US)

(73) Assignee: Toyota Jidosha Kabushiki Kaisha (JP)

( * ) Notice: Subject to any disclaimer, the term of this patent is extended or adjusted under 35 U.S.C. 154(b) by 291 days.

(21) Appl. No.: 10/979,220

(22) Filed: Nov. 3, 2004

(65) Prior Publication Data

US 2006/0094882 A1    May 4, 2006

(51) Int. Cl.
*H01M 8/00* (2006.01)
*C07C 331/00* (2006.01)

(52) U.S. Cl. .......................... 429/12; 564/79

(58) Field of Classification Search ................ 546/347; 548/206, 202, 240, 335.1, 213; 564/79; 429/12
See application file for complete search history.

(56) References Cited

U.S. PATENT DOCUMENTS

2002/0015883 A1   2/2002   Hilarius et al.
2005/0175867 A1*  8/2005   Adachi et al. ................ 429/12

FOREIGN PATENT DOCUMENTS

| JP | 8-259543    | 10/1996  |
| JP | 11-297355   | 10/1999  |
| JP | 2002-187893 | 7/2002   |
| WO | WO03106419  | * 12/2003 |

OTHER PUBLICATIONS

Sun et al., 1998, CAS: 129:122381.*
Matsumoto et al., 2001, CAS: 134:326156.*
Matsumoto et al., 2003, CAS: 139:370962.*
Kakiuchi et al., 2003, CAS: 139:27842.*
Adachi et al., 2003, CAS: 140: 42034.*
Komiya et al., 2004, CAS: 140:324191.*
Matsumoto, et al.; "Air and Moisture Stable Room Temperature Ionic Liquid as a Novel Electrolyte for Electrochemical Devices"; Molten salts, vol. 44, No. 1 (2001); pp. 7-18.
Umemoto, et al.; "Synthesis of 2,2,2-Trifluoroethylated Onium Salts of Nitrogen, Sulfur, and Phosphorus with (2,2,2-Trifluoroethyl)phenyliodonium Triflate"; 1991 The Chemical Society of Japan; Bull. Chem., Soc. Jpn., vol. 64, No. 6; (1991); pp. 2008-2010.
Bonhôte, et al.; "Hydrophobic, Highly Conductive Ambient-Temperature Molten Salts"; Inorg. Chem.,vol. 35, No. 5; (1996); pp. 1168-1178.
Mirzaei, et al.; "Synthesis of 1-Alkyl-1,2,4-triazoles and the Formation of Quaternary 1-Alkyl-4-polyfluoroalkyl-1,2,4-trizaolium Salts Leading to Ionic Liquids"; J. Org. Chem., vol. 67, No. 26; (2002); pp. 9340-9345.
Gupta et al, "Quaternary trialkyl(polyfluoroalkyl)ammonium salts including liquid iodides," Tetrahedron Letters 44 (2003) 9367-9370.

* cited by examiner

Primary Examiner—Rei-tsang Shiao
(74) Attorney, Agent, or Firm—Finnegan, Henderson, Farabow, Garrett & Dunner, LLP

(57) ABSTRACT

Ambient-temperature molten salts of formula (I):

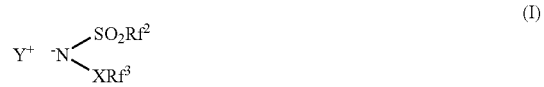

Figure 1:
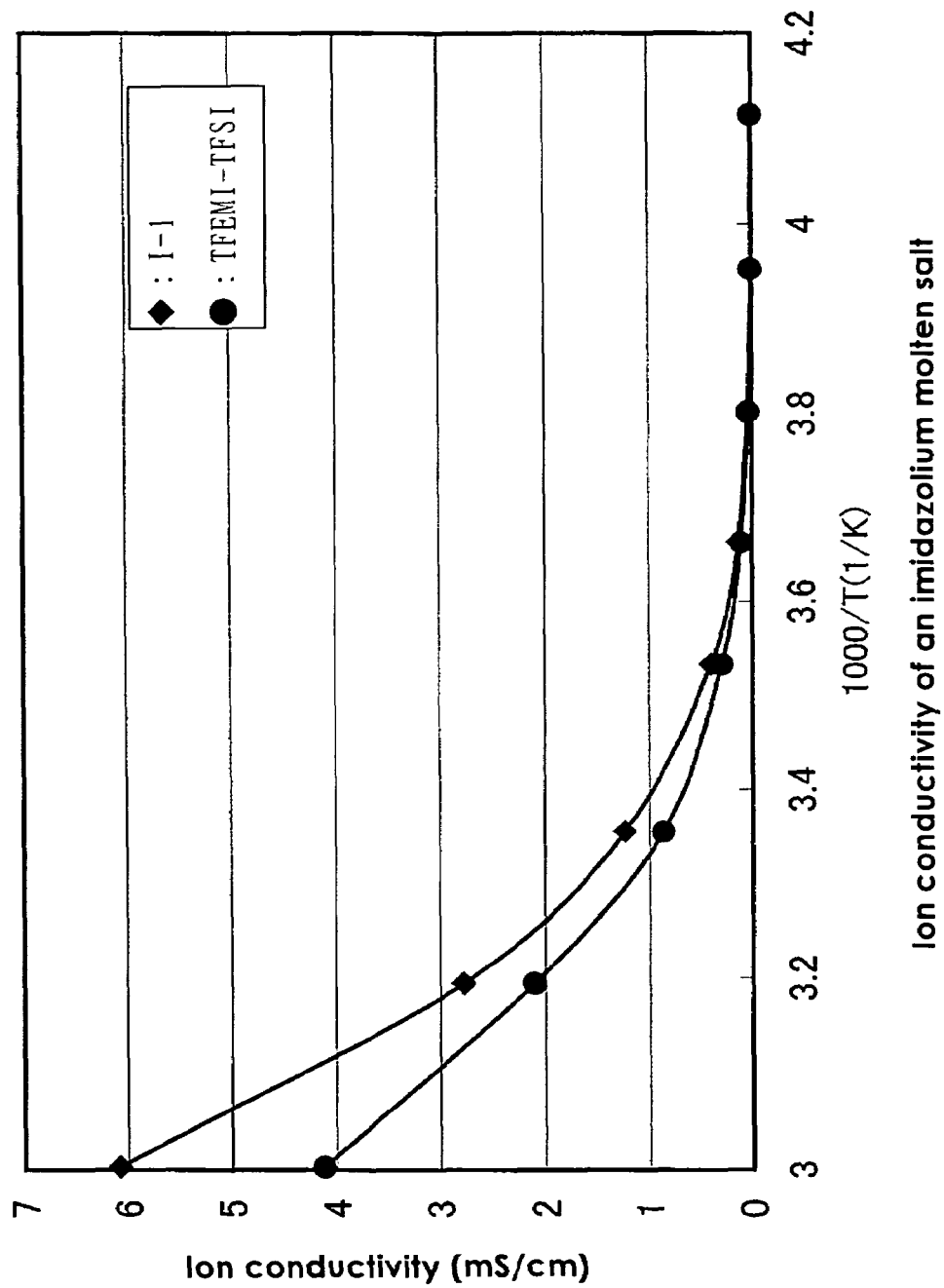

wherein $Y^+$ is a cation selected from the group consisting of an ammonium ion, a sulfonium ion, a pyridinium ion, a(n) (iso)thiazolium ion, and a(n) (iso)oxazolium ion that may be optionally substituted with $C_{1-10}$ alkyl and/or $C_{1-10}$ alkyl having ether linkage, provided that the above cation has at least one substituent of $-CH_2Rf^1$ or $-OCH_2Rf^1$ (wherein $Rf^1$ is $C_{1-10}$ perfluoroalkyl); $Rf^2$ and $Rf^3$ are independently $C_{1-10}$ perfluoroalkyl or may together form $C_{1-4}$ perfluoroalkylene; and X is $-SO_2-$ or $-CO-$.

11 Claims, 1 Drawing Sheet

AMBIENT-TEMPERATURE MOLTEN SALTS AND PROCESS FOR PRODUCING THE SAME

TECHNICAL FIELD

The present invention relates to a compound that is used for producing hydrophobic, highly conductive ambient-temperature molten salts, ionic liquids, or the like that are useful in the field of material science. More particularly, the present invention relates to a novel compound which enables fluoroalkyl and imide anion to be introduced simultaneously and a method for producing the same. Further, the present invention relates to novel ambient-temperature molten salts having wide potential windows and high ion conductivities and a method for producing the same.

BACKGROUND ART

A compound comprising 1-methyl-3-(2', 2', 2'-trifluoroethyl)imidazolium cation and —N(SO$_2$CF$_3$)$_2$ imide anion is known to have fluoroalkyl and imide anion. This compound is useful as hydrophobic, highly conductive ambient-temperature molten salts (Inorganic Chemistry, vol. 35, pp. 1168-1178 (1996)).

A method for producing such 1-methyl-3-(fluoroalkyl)imidazolium imide is known. In this method, fluoroalcohol is allowed to react with trifluoromethanesulfonic anhydride, the reaction product is then allowed to react with 1-methylimidazole to obtain 1-methyl-3-(fluoroalkyl)imidazolium trifluoromethanesulfonate, and the resultant is allowed to react with lithium imide salt to obtain 1-methyl-3-(fluoroalkyl)imidazolium imide by salt exchange (Inorganic Chemistry, vol. 35, pp. 1168-1178 (1996)). This conventional method, however, was seriously deficient from the viewpoints of yield, which was as low as 15% as the total yield from 1-methylimidazole, and difficulty in obtaining a highly purified product.

It was reported that (2,2,2-trifluoroethyl)(phenyl)iodonium bis(trifluoromethanesulfonyl)imide had been synthesized and this could be used as an agent for introducing trifluoroethyl (Chemical Communication, 1998, pp. 2241-2242). However, (2,2,2-trifluoroethyl)(phenyl)iodonium bis(trifluoromethanesulfonyl)imide had low crystallinity, and thus, isolation or purification thereof was disadvantageously complicated.

In the production of (2,2,2-trifluoroethyl)(phenyl)iodonium bis(trifluoromethanesulfonyl)imide, there was only one known suitable reaction solvent, i.e., 1,1,2-trichlorotrifluoroethane (CFC-113) (Chemical Communication, 1998, pp. 2241-2242). CFC-113, however, was an ozone depleting substance and had caused severe environmental destruction. Thus, industrialization thereof was difficult.

Although fluoroalkylaryliodonium sulfonate is known (Bulletin of the Chemical Society of Japan, vol. 60, pp. 3307-3313 (1987) and U.S. Pat. No. 4,873,027 (JP Patent Publication (Kokoku) No. 3-58332 B (1991)), fluoroalkyl and imide anion cannot be simultaneously introduced with the use of this compound.

As described above, there was no method that could simultaneously and efficiently introduce fluoroalkyl and imide anion.

Recently, triazolium imide salt having Rf'CH$_2$CH$_2$— (wherein Rf' is C$_{1-6}$ perfluoroalkyl) has been reported as an ambient-temperature molten salt (Journal of Organic Chemistry, Vol. 67. pp. 9340-9345(2002)). However, triazole compound as a starting material is expensive and it requires at least three reaction steps.

Further, ammonium imide salt having Rf"CH$_2$CH$_2$— (wherein Rf" is C$_{4-10}$ perfluoroalkyl) has been reported (Tetrahedron Letters, Vol. 44. pp. 9367-9370(2003)). However, it requires two reaction steps to synthesize the ammonium imide salt having Rf"CH$_2$CH$_2$—.

DISCLOSURE OF THE INVENTION

Objects of the present invention are to provide a compound that enables fluoroalkyl and imide anion to be simultaneously and highly efficiently introduced, a method for easily producing ambient-temperature molten salts with high yield using the aforementioned compound, and novel ambient-temperature molten salts having wide potential windows and high ion conductivities.

The present inventors have conducted concentrated studies in order to overcome the aforementioned drawbacks. As a result, they have found that fluoroalkyl and imide anion can be easily, simultaneously, and highly efficiently introduced in a single step with the use of a fluoroalkylaryliodonium imide compound. This has led to the completion of the present invention.

More specifically, the present invention includes the following inventions.

(1) Ambient-temperature molten salts of formula (I):

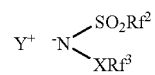

wherein,

Y$^+$ is a cation selected from the group consisting of an ammonium ion, a sulfonium ion, a pyridinium ion, a(n) (iso)thiazolium ion, and/or a(n) (iso)oxazolium ion, which may be optionally substituted with C$_{1-10}$ alkyl and/or C$_{1-10}$ alkyl having ether linkage, provided that said cation has at least one substituent of —CH$_2$Rf$^1$ or —OCH$_2$Rf$^1$ (wherein Rf$^1$ is C$_{1-10}$ perfluoroalkyl);

Rf$^2$ and Rf$^3$ are independently C$_{1-10}$ perfluoroalkyl or may together form C$_{1-4}$ perfluoroalkylene; and, X is —SO$_2$— or —CO—.

(2) The ambient-temperature molten salts according to (1) above, wherein Y$^+$ is an ammonium ion of formula (II):

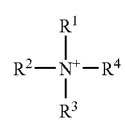

wherein R$^1$ to R$^4$ are independently hydrogen atom, C$_{1-10}$ alkyl, C$_{1-10}$ alkyl having ether linkage, —CH$_2$Rf$^1$, or —OCH$_2$Rf$^1$ (wherein Rf$^1$ is C$_{1-10}$ perfluoroalkyl) or two of R$^1$ to R$^4$ may together form a morpholine, piperidine, or pyrrolidine ring, provided that at least one of Rf$^1$ to R$^4$ is —CH$_2$Rf$^1$ or —OCH$_2$Rf$^1$.

(3) The ambient-temperature molten salts according to (1) above, wherein $Y^+$ is a sulfonium ion of formula (III):

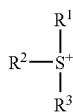
(III)

wherein $R^1$ to $R^3$ are independently hydrogen atom, $C_{1-10}$ alkyl, $C_{1-10}$ alkyl having ether linkage, or —$CH_2Rf^1$ (wherein $Rf^1$ is $C_{1-10}$ perfluoroalkyl), provided that at least one of $R^1$ to $R^3$ is —$CH_2Rf^1$.

(4) The ambient-temperature molten salts according to (1) above, wherein $Y^+$ is a pyridinium ion of formula (IV):

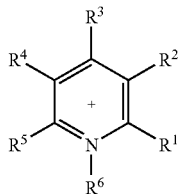
(IV)

wherein $R^1$ to $R^5$ are independently hydrogen atom, $C_{1-10}$ alkyl, $C_{1-10}$ alkyl having ether linkage, —$CH_2Rf^1$, or —$OCH_2Rf^1$ (wherein $Rf^1$ is $C_{1-10}$ perfluoroalkyl), and $R^6$ is —$CH_2Rf^1$ or —$OCH_2Rf^1$.

(5) The ambient-temperature molten salts according to (1) above, wherein $Y^+$ is a(n) (iso)thiazolium ion or (iso)oxazolium ion of formula (V):

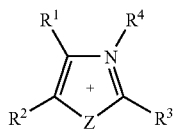 or 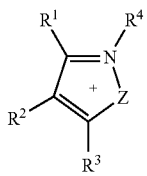
(V)

wherein $R^1$ to $R^3$ are independently hydrogen atom, $C_{1-10}$ alkyl, $C_{1-10}$ alkyl having ether linkage, or —$CH_2Rf^1$ (wherein $Rf^1$ is $C_{1-10}$ perfluoroalkyl), $R^4$ is —$CH_2Rf^1$, and Z is an oxygen or sulfur atom.

(6) Ambient-temperature molten salts of formula (VI):

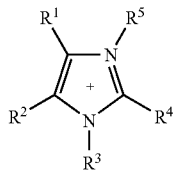 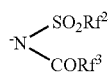
(VI)

wherein $R^1$ to $R^5$ are independently hydrogen atom, $C_{1-10}$ alkyl, $C_{1-10}$ alkyl having ether linkage, or —$CH_2Rf^1$ (wherein $Rf^1$ is $C_{1-10}$ perfluoroalkyl), provided that at least one of $R^3$ or $R^5$ is —$CH_2Rf^1$, $Rf^2$ and $Rf^3$ are independently $C_{1-10}$ perfluoroalkyl or may together form $C_{1-4}$ perfluoroalkylene.

(7) A fluoroalkylfluorophenyliodonium imide compound of formula (VII):

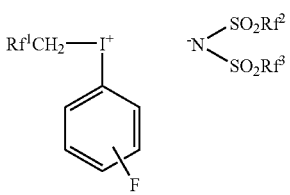
(VII)

wherein $Rf^1$ is $C_{1-10}$ perfluoroalkyl, $Rf^2$ and $Rf^3$ are independently $C_{1-10}$ perfluoroalkyl or together form $C_{1-4}$ perfluoroalkylene.

(8) A method for producing a compound of formula (VIII):

$$Y'^+ \quad {}^-N{\overset{SO_2Rf^2}{\underset{SO_2Rf^3}{\diagdown}}}$$
(VIII)

wherein $Y'^+$ is a cation selected from the group consisting of an imidazolium ion, an ammonium ion, a sulfonium ion, a pyridinium ion, a(n) (iso)thiazolium ion, and a(n) (iso)oxazolium ion, which may be optionally substituted with $C_{1-10}$ alkyl and/or $C_{1-10}$ alkyl having ether linkage, provided that said cation has at least one substituent of —$CH_2Rf^1$ or —$OCH_2Rf^1$ (wherein $Rf^1$ is $C_{1-10}$ perfluoroalkyl); and, $Rf^2$ and $Rf^3$ are independently $C_{1-10}$ perfluoroalkyl or may together form $C_{1-4}$ perfluoroalkylene, which comprises reacting a heteroatom-containing compound selected from the group consisting of imidazole, amine, amine N-oxide, sulfide, pyridine, pyridine N-oxide, (iso)thiazole, and (iso)oxazole, which may be optionally substituted with $C_{1-10}$ alkyl, $C_{1-10}$ alkyl having ether linkage, —$CH_2Rf^1$ and/or —$OCH_2Rf^1$ (wherein $Rf^1$ is $C_{1-10}$ perfluoroalkyl), with a fluoroalkylaryliodonium imide compound of formula (IX):

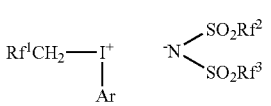
(IX)

wherein $Rf^1$, $Rf^2$, and $Rf^3$ are as defined above, and Ar is unsubstituted phenyl or phenyl that may be optionally substituted with halogen atom or $C_{1-10}$ alkyl, to give a compound of formula (VIII).

(9) The production method according to (8) above, wherein —Ar is phenyl or represented by the following formula:

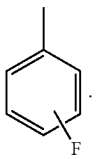

(10) The production method according to (8) above, wherein —Ar is represented by the following formula:

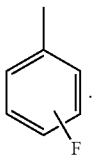

The present invention is hereafter described in detail.

The term "$C_{1-10}$ alkyl" used herein refers to a straight-chain or branched alkyl group having 1 to 10 carbon atoms. Examples thereof include methyl, ethyl, n-propyl, isopropyl, n-butyl, isobutyl, tert-butyl, n-pentyl, n-hexyl, n-heptyl, n-octyl, n-nonyl, and n-decyl.

The term "$C_{1-10}$ perfluoroalkyl" used herein refers to an alkyl group as defined above in which all hydrogen atoms are substituted with fluorine atoms. Examples thereof include, for example, $CF_3-$, $CF_3CF_2-$, $CF_3(CF_2)_2-$, $CF_3(CF_2)_3-$, $CF_3(CF_2)_4-$, $CF_3(CF_2)_5-$, $CF_3(CF_2)_6-$, $CF_3(CF_2)_7-$, $CF_3(CF_2)_8-$, $CF_3(CF_2)_9-$, $(CF_3)_2CF-$, and $(CF_3CF_2)(CF_3)CF-$, $(CF_3)_2CFCF_2-$, $(CF_3)_2CFCF_2CF_2-$.

Ambient-temperature molten salts compound of formula (I) according to the present invention is now described:

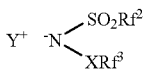

(I)

wherein $Y^+$ is a cation selected from a group consisting of ammonium ion, sulfonium ion, pyridinium ion, (iso)thiazolium ion and (iso)oxazolium ion, which may be optionally substituted with $C_{1-10}$ alkyl and/or $C_{1-10}$ alkyl having ether linkage, provided that said cation has at least one substituent of $-CH_2Rf^1$ or $-OCH_2Rf^1$ (wherein $Rf^1$ is $C_{1-10}$ perfluoroalkyl); $Rf^2$ and $Rf^3$ are independently $C_{1-10}$ perfluoroalkyl or may together form $C_{1-4}$ perfluoroalkylene; and X is $-SO_2-$ or $-CO-$.

$Rf^1$ is $C_{1-10}$ perfluoroalkyl, more preferably $C_{1-7}$ perfluoroalkyl, and further preferably $C_{1-4}$ perfluoroalkyl.

$Rf^2$ and $Rf^3$ may independently be any combinations of $C_{1-10}$ perfluoroalkyls as exemplified above. More preferably, $Rf^2$ and $Rf^3$ are independently combinations of perfluoroalkyls, such as $^-N(SO_2CF_3)_2$, $^-N(SO_2CF_3)(SO_2C_2F_5)$, $^-N(SO_2C_2F_5)_2$, $^-N(SO_2C_3F_7)_2$, $^-N(SO_2C_4F_9)_2$, $^-N(SO_2CF_3)(SO_2C_4F_9)$, $^-N(SO_2CF_3)(SO_2C_6F_{13})$, $^-N(SO_2CF_3)(SO_2C_8F_{17})$, or $^-N(SO_2C_4F_9)(SO_2C_6F_{13})$.

Furthermore, $Rf^2$ and $Rf^3$ may independently be any combinations of $C_{1-7}$ perfluoroalkyls, more preferably $C_{1-4}$ perfluoroalkyls.

Alternatively, $Rf^2$ and $Rf^3$ may together form $C_{1-4}$ perfluoroalkylene. In such a case, an imide anion portion forms a cyclic structure as shown below.

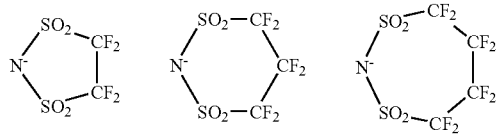

An example of $C_{1-4}$ perfluoroalkylene is straight chain or branched $C_1C_4$ perfluoroalkylene. $-CF_2-$, $-CF_2CF_2-$, $-CF(CF_3)CF_2-$, $-CF_2CF_2CF_2-$, $-CF_2CF_2CF_2CF_2-$, or the like is preferable.

Examples of a cation of a hetero atom-containing compound represented by $Y^+$, which may be optionally substituted with $C_{1-10}$ alkyl and/or $C_{1-10}$ alkyl having ether linkage, include cations derived from amine, amine N-oxide, sulfide, pyridine, pyridine N-oxide, (iso)thiazole, and (iso)oxazole. Specific examples are ammonium ion, sulfonium ion, pyridinium ion, (iso)thiazolium ion, and (iso)oxazolium ion. It should be noted that these cations have at least one substituent of $-CH_2Rf^1$ or $-OCH_2Rf^1$ (wherein $Rf^1$ is $C_{1-10}$, preferably $C_{1-7}$, and more preferably $C_{1-4}$ perfluoroalkyl).

$Y^+$ is preferably a cation selected from the following:

an ammonium ion of formula (II):

(II)

wherein $Rf^1$ to $R^4$ are independently hydrogen atom, $C_{1-10}$ alkyl, $C_{1-10}$ alkyl having ether linkage, $-CH_2Rf^1$, or $-OCH_2Rf^1$ (wherein $Rf^1$ is as defined above) or two of $Rf^1$ to $R^4$ may together form a morpholine, piperidine, or pyrrolidine ring, provided that at least one of $Rf^1$ to $R^4$ is $-CH_2Rf^1$ or $-OCH_2Rf^1$;

a sulfonium ion of formula (III):

(III)

wherein $Rf^1$ to $R^3$ are independently hydrogen atom, $C_{1-10}$ alkyl, $C_{1-10}$ alkyl having ether linkage, or $-CH_2Rf^1$ (wherein $Rf^1$ is as defined above), provided that at least one of $Rf^1$ to $R^3$ is $-CH_2Rf^1$;

a pyridinium ion of formula (IV):

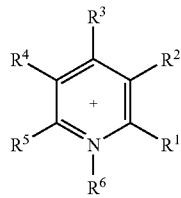

(IV)

wherein $Rf^1$ to $R^5$ are independently hydrogen atom, $C_{1-10}$ alkyl, $C_{1-10}$ alkyl having ether linkage, —$CH_2Rf^1$, or —$OCH_2Rf^1$ (wherein $Rf^1$ is as defined above), and $R^6$ is —$CH_2Rf^1$ or —$OCH_2Rf^1$; and a(n) (iso)thiazolium ion or (iso)oxazolium ion of formula (V):

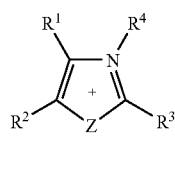 or 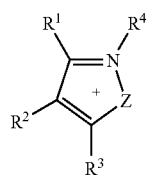

(V)

wherein $R^1$ to $R^3$ are independently hydrogen atom, $C_{1-10}$ alkyl, $C_{1-10}$ alkyl having ether linkage, or —$CH_2Rf^1$ (wherein $Rf^1$ is as defined above), $R^4$ is —$CH_2Rf^1$, and Z is an oxygen or sulfur atom.

An anion portion in a compound of formula (I) preferably has an asymmetric structure. In other words, —$SO_2Rf^2$ and —$XRf^3$ are preferably not identical to each other.

Furthermore, the present invention includes the ambient-temperature molten salts of formula (VI):

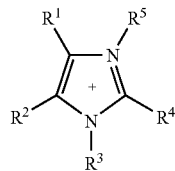 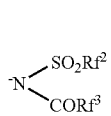

(VI)

wherein $R^1$ to $R^5$ are independently hydrogen atom, $C_{1-10}$ alkyl, $C_{1-10}$ alkyl having ether linkage, or —$CH_2Rf^1$ (wherein $Rf^1$ is $C_{1-10}$, preferably $C_{1-7}$, and more preferably $C_{1-4}$ perfluoroalkyl), provided that at least one of $R^3$ or $R^1$ is —$CH_2Rf^1$, $Rf^2$ and $Rf^3$ are independently $C_{1-10}$, preferably $C_{1-7}$, and more preferably $C_{1-4}$ perfluoroalkyl or may together form $C_{1-4}$ perfluoroalkylene.

The melting point of the ambient-temperature molten salts of formulae (I) and (VI) is low, and is generally ambient temperature or lower. "Ambient-temperature" refers to temperature under circumstances without any special heating and cooling and is, for example, about 25° C. Even though a salt has a melting point of ambient temperature or higher (e.g., about 100° C.), it may exist in a liquid state (a supercooled liquid) at ambient temperature due to the supercooling phenomenon. The term "ambient-temperature molten salts" used herein refers to not only salts having a melting point of ambient temperature or lower but also salts that can exist in a liquid state (a supercooled liquid) at ambient temperature or lower even though its melting point is ambient temperature or higher.

The ambient-temperature molten salts of formulae (I) and (VI) have high conductivities, wide potential windows, incombustibility, and nonvolatile properties. Thus, they are useful compounds for electrolytes for lithium cells or the like.

A method for producing the ambient-temperature molten salts of formula (I') is then described:

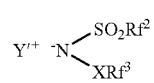

(I')

wherein $Y'^+$, $Rf^2$, $Rf^3$, and X are as defined above.

The ambient-temperature molten salt compound of formula (I') wherein X is —$SO_2$— can be produced by allowing a compound of formula (IX):

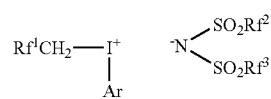

(IX)

(wherein Ar is unsubstituted phenyl or phenyl that may be optionally substituted with halogen atom or $C_{1-10}$ alkyl, and $Rf^1$, $Rf^2$, and $Rf^3$ are as defined above) to react with a hetero atom-containing compound selected from a group consisting of imidazole, amine, amine N-oxide, sulfide, pyridine, pyridine N-oxide, (iso)thiazole and (iso)oxazole.

Ar denotes substituted or unsubstituted phenyl. When it is substituted phenyl, examples of substituents include halogen atom and $C_{1-10}$ alkyl. Examples of halogen atom include fluorine, chlorine, bromine, and iodine atom, with fluorine atom being preferable. An example of $C_{1-10}$ alkyl is the aforementioned alkyl, and it is preferably $C_{1-4}$ alkyl such as methyl, ethyl, n-propyl, isopropyl, n-butyl, isobutyl, or tert-butyl. Unsubstituted phenyl and fluorophenyl are particularly preferable from the viewpoints of reaction efficiency, yield, and stability. Fluorophenyl is more preferable from the viewpoints of easy isolation and purification in the production process of the starting compound of formula (IX) and simultaneous production of useful fluoroiodobenzene as described later.

Hetero atom-containing compounds may be substituted with $C_{1-10}$ alkyl, $C_{1-10}$ alkyl having ether linkage, —$CH_2Rf^1$, and/or —$OCH_2Rf^1$ (wherein $Rf^1$ is as defined above). The term "$C_{1-10}$ alkyl having ether linkage" used herein refers to "$C_{1-10}$ alkyl" as defined above, which contains at least one ether linkage (—O—) in its alkyl chain. Examples thereof include $CH_3O$—, $CH_3OCH_2$—, $CH_3O(CH_2)_2$—, $CH_3CH_2OCH_2$—, $CH_3CH_2OCH_2CH_2$—, $CH_3O(CH_2)_3$—, $CH_3CH_2O(CH_2)_3$—, and $CH_3O(CH_2)_2O(CH_2)_2O$—. Such alkyl having ether linkage may be substituted with fluorine atom (e.g. $CF_3CH_2OCH_2CH_2$—).

Hetero atom-containing compounds as used herein are commercially available or may be prepared by known method. The hetero atom-containing compounds having —$CH_2Rf^1$ or —$OCH_2Rf^1$ substituent may be prepared, for example, by employing $Rf^1CH_2I^+(Ph)TfO^-$ (TfO⁻: trifluoromethanesulfonate anion) as introducing agent for —CH$_2$Rf$^1$ (see, Journal of Fluorine Chemistry, 31, pp. 231-236(1986)).

In the reaction between the compound of formula (IX) and a hetero atom-containing compound, the amount of the hetero atom-containing compound to be used is generally between 0.2 moles and 2 moles relative to 1 mole of the compound of formula (IX). It is preferably between 0.3 and 1.5 moles from the viewpoints of economical efficiency and yield.

The compound of formula (IX) is generally allowed to react with a hetero atom-containing compound in a solvent. When the hetero atom-containing compound is liquid, the reaction can be carried out without the use of a solvent. Examples of a solvent that is used in the aforementioned reaction include: chloroalkanes, such as methylene chloride, chloroform, carbon tetrachloride, dichloroethane, trichloroethane, or tetrachloroethane; fluorochloroalkanes, such as trichlorotrifluoroethane; aromatic compounds, such as benzene, chlorobenzene, fluorobenzene, or toluene; ethers, such as diethyl ether, dipropyl ether, diisopropyl ether, tetrahydrofuran, or dioxane; nitriles, such as acetonitrile or propionitrile; nitro compounds, such as nitromethane, nitroethane, or nitrobenzene; water; alcohols, such as methanol, ethanol, propanol, isopropanol, butanol, sec-butanol, or t-butanol; and mixtures thereof. Among these solvents, use of carbon tetrachloride or fluorochloroalkane is preferably refrained from the environmental problem of ozone depletion.

The reaction temperature varies depending on reactivity of a hetero atom-containing compound to be used. It is generally between −80° C. and +100° C., and it is preferably between −50° C. and +80° C. in order to proceed the reaction with high yield and efficiency.

A compound of formula (VII):

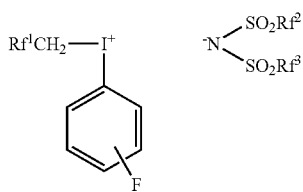

(VII)

(wherein Rf$^1$, Rf$^2$ and Rf$^3$ are as defined above) that is used in the above production method is novel.

When a compound of formula (VII) is used as starting material for preparing an ambient-temperature molten salt of formula (I'), fluoroiodobenzene is produced together. Fluoroiodobenzene is an important intermediate for producing medicines or agrochemicals (see CA 85-108420f). Thus, a compound of formula (VII) according to the present invention is a useful not only for introducing fluoroalkyl Rf$^1$CH$_2$— (Rf$^1$ is as defined above) easily together with imide anion N$^-$(SO$_2$Rf$^2$)(SO$_2$Rf$^3$)(Rf$^2$ and Rf$^3$ are as defined above) in one reaction step, but also for producing fluoroiodobenzene, which is important as medicinal and agrochemical intermediate, in good yield.

Negative charge in the anion portion of the compound of formulae (IX) and (VII) is not localized in a nitrogen atom. The anion portion has a resonance structure as shown below.

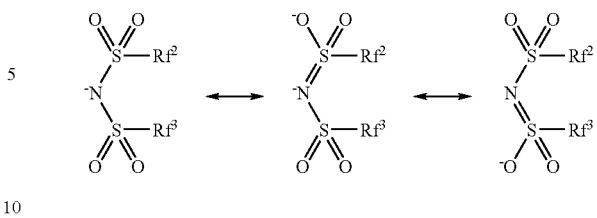

The fluoroalkylaryliodonium imide compound of formula (IX) according to the present invention can be produced in the following manner.

The compound of formula (IX) can be produced by allowing a fluoroalkyl iodoso compound of formula (X):

(X)

(wherein Rf$^1$ is as defined above and Rf$^4$ is C$_{1-4}$ perfluoroalkyl) to react with Ar—H (wherein Ar is as defined above) and with an imide compound of formula (XI):

(XI)

(wherein Rf$^2$ and Rf$^3$ are as defined above).

In formula (X), Rf$^4$ is C$_{1-4}$ perfluoroalkyl, and examples thereof include CF$_3$—, CF$_3$CF$_2$—, CF$_3$(CF$_2$)$_2$—, (CF$_3$)$_2$CF—, CF$_3$(CF$_2$)$_3$—, (CF$_3$CF$_2$)(CF$_3$)CF—, (CF$_3$)$_2$CFCF$_2$—, and (CF$_3$)$_3$C—.

The iodoso compound of formula (X) can be produced from commercially available iodofluoroalkane by a conventional technique. For example, it can be easily produced by allowing iodofluoroalkane: Rf$^1$CH$_2$I (wherein Rf$^1$ is as defined above) to react with perfluoroalkyl peroxy carboxylic acid: Rf$^4$COOOH (wherein Rf$^4$ is as defined above) (for example, Bulletin of the chemical Society of Japan, vol. 60, pp. 3307-3313 (1987)). For example, perfluoroalkyl peroxy carboxylic acid: Rf$^4$COOOH can be easily produced by allowing a 20% to 60% hydrogen peroxide solution to react with perfluoroalkyl carboxylic anhydride: (Rf$^4$CO)$_2$O in the presence of perfluoroalkyl carboxylic acid: Rf$^4$COOH.

Alternatively, the iodoso compound of formula (X) can be obtained by chlorinating iodofluoroalkane: Rf$^1$CH$_2$I (wherein Rf$^1$ is as defined above) using chlorine gas and then processing it with silver salt of perfluoroalkyl carboxylic acid (Tetrahedron Letters, vol. 35 (No. 43), pp. 8015-8018 (1994)).

Examples of iodoso compounds of formula (X) that are used in this reaction include CF$_3$CH$_2$I(OCOCF$_3$)$_2$, CF$_3$CH$_2$I(OCOC$_2$F$_5$)$_2$, CF$_3$CH$_2$I(OCOC$_3$F$_7$)$_2$, CF$_3$CH$_2$I(OCOC$_4$F$_9$)$_2$, CF$_3$CF$_2$CH$_2$I(OCOCF$_3$)$_2$, CF$_3$(CF$_2$)$_2$CH$_2$I(OCOCF$_3$)$_2$, CF$_3$(CF$_2$)$_3$CH$_2$I(OCOCF$_3$)$_2$, CF(CF$_2$)$_4$CH$_2$I(OCOCF$_3$)$_2$, CF$_3$(CF$_2$)$_5$CH$_2$I(OCOCF$_3$)$_2$, CF$_3$(CF$_2$)$_6$CH$_2$I(OCOCF$_3$)$_2$, CF$_3$(CF$_2$)$_7$CH$_2$I(OCOCF$_3$)$_2$, CF$_3$(CF$_2$)$_8$CH$_2$I(OCOCF$_3$)$_2$, CF$_3$(CF$_2$)$_9$CH$_2$I(OCOCF$_3$)$_2$, (CF$_3$)$_2$CFCH$_2$I(OCOCF$_3$)$_2$, (CF$_3$CF$_2$)(CF$_3$)CFCH$_2$I(OCOCF$_3$)$_2$, (CF$_3$)$_2$CFCF$_2$CH$_2$I(OCOCF$_3$)$_2$, and (CF$_3$)$_2$CFCF$_2$CF$_2$CH$_2$I(OCOCF$_3$)$_2$, CF$_3$CH$_2$I(OCOCF$_3$)$_2$, CF$_3$CF$_2$CH$_2$I(OCOCF$_3$)$_2$, CF$_3$(CF$_2$)$_2$CH$_2$I(OCOCF$_3$)$_2$, CF$_3$(CF$_2$)$_3$CH$_2$I(OCOCF$_3$)$_2$, CF$_3$(CF$_2$)$_4$CH$_2$I(OCOCF$_3$)$_2$, CF$_3$(CF$_2$)$_5$CH$_2$I(OCOCF$_3$)$_2$, CF$_3$(CF$_2$)$_6$CH$_2$I(OCOCF$_3$)$_2$, CF$_3$(CF$_2$)$_7$CH$_2$I(OCOCF$_3$)$_2$, CF$_3$(CF$_2$)$_8$CH$_2$I(OCOCF$_3$)$_2$, CF$_3$(CF$_2$)$_9$CH$_2$I(OCOCF$_3$)$_2$, (CF$_3$)$_2$ $CFCH_2I(OCOCF_3)_2$, $(CF_3)_2CFCF_2CH_2I(OCOCF_3)_2$, $(CF_3)_2CFCF_2CF_2CH_2I(OCOCF_3)_2$, and the like are preferable.

A starting material, unsubstituted benzene or benzene Ar—H that may be optionally substituted with halogen atom or $C_{1-10}$ alkyl, is commercially available.

Imide of formula (XI) is commercially available or can be easily produced by conventional techniques (for example, Inorganic Chemistry, vol. 23, pp. 3720-3723 (1984); Chem. Ztg., vol. 96, p. 582 (1972); and JP Patent Publication (Kokai) No. 62-26264 A (1987)).

The stoichiometric ratios of an iodoso compound (X), a benzene compound Ar—H, and an imide compound (XI) that are used as starting materials are as follows.

The amount of Ar—H to be used is generally 0.8 to 10 moles relative to 1 mole of the iodoso compound of formula (X), and it is preferably 0.9 to 2 moles from the viewpoints of economical efficiency and yield. The amount of the imide compound of formula (XI) to be used is generally 0.7 to 2 moles relative to 1 mole of the iodoso compound of formula (X), and it is preferably 0.8 to 1.5 moles, and more preferably 0.9 to 1.2 moles from the viewpoints of economical efficiency and yield.

The aforementioned starting material is allowed to react in a solvent at temperature from −90° C. to +50° C., and preferably from −30° C. to room temperature.

Examples of solvents include: chloroalkanes, such as methylene chloride, chloroform, carbon tetrachloride, dichloroethane, and trichloroethane; fluorochloroalkanes, such as trichlorofluoromethane, trichlorofluoroethane, and trichlorotrifluoroethane; halogenated fatty acids, such as trifluoroacetic acid, chlorodifluoroacetic acid, pentafluoropropionic acid, and heptafluorobutyric acid; halogenated fatty acid anhydrides, such as trifluoroacetic anhydride, chlorodifluoroacetic anhydride, pentafluoropropionic anhydride, and heptafluorobutyric anhydride; and mixtures thereof. Chloroalkanes or fluorochloroalkanes are preferable in terms of simple handleability. In order to avoid the environmental problem of ozone depletion, chloroalkanes excluding carbon tetrachloride are particularly preferable. Further, methylene chloride is most preferable from the viewpoints of yield, efficiency, and recovery that is necessary for avoiding the environmental problem.

The amount of a solvent to be used is generally 100 liters or smaller, and preferably 10 liters or smaller, relative to 1 mole of the fluoroalkyl iodoso compound of formula (X). It is particularly preferably 5 litters or smaller from the viewpoint of economical efficiency. The minimal amount of a solvent is not particularly limited, and the amount, with which the reaction efficiently proceeds, is adequately selected.

The reaction period may be adequately determined depending on a starting material, a solvent, reaction temperature, or the like to be employed. It is generally between 5 minutes and 60 hours, and preferably between 30 minutes and 30 hours.

After the completion of the reaction, the reaction product is subjected to general post-treatment and then purified by a technique known to persons skilled in the art, such as recrystallization, to obtain a subject compound of formula (IX).

A compound of formula (IX) wherein Ar is fluorophenyl is a fluoroalkylfluorophenyliodonium imide compound of formula (VII), which is produced by using fluorobenzene as Ar—H. A fluoroalkylfluorophenyliodonium imide compound of formula (VII) has particularly high crystallinity, and it can be easily isolated and purified by recrystallization. For example, while the melting point of (2,2,2-trifluoroethyl)(phenyl)iodonium imide is between 76° C. and 78° C. (see Example 7), that of (2,2,2-trifluoroethyl)(p-fluorophenyl)iodonium imide is high, i.e., between 98.5° C. and 100° C. (see Example 1). (2,2,3,3,3-Pentafluoropropyl)(phenyl)iodonium imide is an oily amorphous substance at room temperature (see Example 8). In contrast, the melting point of (2,2,3,3,3-pentafluoropropyl)(p-fluorophenyl)iodonium imide is surprisingly a crystalline substance having a high melting point between 91° C. and 93° C/ (see Example 3).

A compound (I) wherein X is —CO— or —SO$_2$— and a compound (VI) can be produced by salt exchange. Salt exchange is a known technique and can be carried out in accordance with the method described in, for example, Inorganic Chemistry, vol. 35, pp. 1168-1178 (1996) or Journal of Physical Chemistry, B, vol. 102, pp. 8858-8864 (1998).

When a compound is produced by salt exchange, a salt selected from the group consisting of imidazolium salt, ammonium salt, sulfonium salt, pyridinium salt, (iso)thiazolium salt, and (iso)oxazolium salt that may be optionally substituted with $C_{1-10}$ alkyl and/or $C_{1-10}$ alkyl having ether linkage, provided that the above cation has at least one substituent of —CH$_2$Rf$^1$ or —OCH$_2$Rf$^1$ (wherein Rf$^1$ is as defined above) is allowed to react with a salt of formula (XII):

(XII)

(wherein Rf$^2$ and Rf$^3$ are as defined above, X is —CO— or —SO$_2$—, and M$^+$ is a monovalent metal ion, such as Li$^+$, Na$^+$, or K$^+$).

Preferable examples of imidazolium salt, ammonium salt, sulfonium salt, pyridinium salt, (iso)thiazolium salt, and (iso)oxazolium salt that has at least one substituent of —CH$_2$Rf$^1$ or —OCH$_2$Rf$^1$ (wherein Rf$^1$ is as defined above) and may be optionally substituted with $C_{1-10}$ alkyl and/or $C_{1-10}$ alkyl having ether linkage include salts of a cation represented by Y$^{r+}$ as mentioned above (e.g., an imidazolium, ammonium, sulfonium, pyridinium, (iso)thiazolium, or (iso)oxazolium ion) with an anion (e.g., trifluoromethanesulfonate anion, TfO$^-$). These salts can be produced by conventional techniques. For example, R$^a$R$^b$R$^c$N$^+$CH$_2$Rf$^1$ •TfO$^-$ (wherein R$^a$, R$^b$, and R$^c$ are independently $C_{1-10}$ alkyl, $C_{1-10}$ alkyl having ether linkage, —CH$_2$Rf$^1$ or —OCH$_2$Rf$^1$ (wherein Rf$^1$ is as defined above)) can be produced by allowing amine R$^a$R$^b$R$^c$N to react with Rf$^1$CH$_2$I$^+$(Ph)TfO$^-$ (Bulletin of the Chemical Society of Japan, vol. 64, pp. 2008-2010 (1991)).

Salt exchange between the aforementioned salt and the salt of formula (XII) can exchange salt anion with imide anion N$^-$(SO$_2$Rf$^2$)(XRf$^3$) (wherein Rf$^2$, Rf$^3$, and X are as defined above). Thus, a compound of formula (I) or (VI) can be obtained.

BEST MODES FOR CARRYING OUT THE INVENTION

The present invention is hereafter described in more detail with reference to the following examples, although the scope of the present invention is not limited to these examples.

EXAMPLE 1

Production of (fluoroalkyl)(fluorophenyl)iodonium imide

Compound 1

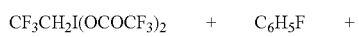
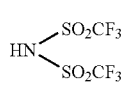
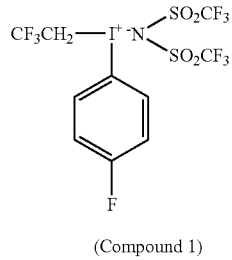

(Compound 1)

$CF_3CH_2I(OCOCF_3)_2$ (43.6 g, 100 mmol), $HN(SO_2CF_3)_2$ (28.1 g, 100 mmol), and dried methylene chloride (125 ml) were placed in a reaction vessel, the content of the reaction vessel was subjected to nitrogen substitution, and the mixed solution was stirred at room temperature for 30 minutes. The resultant was cooled in a bath at 0° C., and fluorobenzene (14.2 ml, 150 mmol) was then added dropwise thereto while stirring over the course of 2 minutes. Thereafter, the temperature of the bath was slowly raised to room temperature, and the mixture was allowed to react at room temperature for 20 hours.

After the completion of the reaction, the solvent was removed by distillation using an evaporator at room temperature, and trifluoroacetic acid as a side product was then removed by sucking with a vacuum pump. The obtained crystalline product was dissolved in a minimal amount of acetonitrile, and chloroform/ether was added thereto. A crystal was precipitated immediately thereafter. The precipitated crystal was separated by filtration, and (2,2,2-trifluoroethyl)(4-fluorophenyl)iodonium bis(trifluoromethanesulfonyl) imide (compound 1) was obtained (yield: 47 g, 80%). A sample for analysis was obtained by being recrystallized from acetonitrile/chloroform.

Melting point: 98.5-100° C. $^1$H-NMR (in $CD_3CN$, ppm): δ 8.15 (dd, J=6, 4 Hz, o-H), 7.35 (t, J=8 Hz, m-H), 4.75 (q, J=10 Hz, $CH_2$) $^{19}$F-NMR (internal standard: $C_6F_6$, in $CD_3CN$, ppm): δ 101.3 (t, J=10 Hz, $CF_3$), 84.3 (s, $CF_3S$), 59.9 (m, p-F) IR (cm$^{-1}$): 1201 ($SO_2$), 1359 ($SO_2$) Elemental analysis: found: C, 20.52%; H, 1.18%; N, 2.40%. calculated: C, 20.53%; H, 1.03%; N, 2.39%.

EXAMPLE 2

Production of (fluoroalkyl)(fluorophenyl)iodonium imide

Compound 2

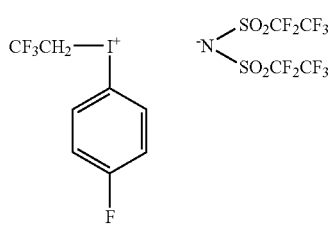

(Compound 2)

Compound 2 was obtained in the same manner as in Example 1, except for the use of $CF_3CH_2I(OCOCF_3)_2$ (21.8 g, 50 mmol), fluorobenzene (7.05 ml, 75 mmol), and $HN(SO_2CF_2CF_3)_2$ (19.1 g, 50 mmol) as starting materials and $CClF_2CCl_2F$ (100 ml) as a solvent (yield 56%).

Melting point: 79.5-80.5° C. $^1$H-NMR (in $CD_3CN$, ppm): δ 8.15 (dd, J=9, 5 Hz, o-H), 7.36 (t, J=9 Hz, m-H), 4.76 (q, J=10 Hz, $CH_2$) $^{19}$F-NMR (internal standard: $C_6F_6$, in $CD_3CN$, ppm): δ 101.4 (t, J=10 Hz, $CF_3CH_2$), 84.5 (s, $CF_3$), 60.0 (m, p-F), 46.2 (s, $CF_2S$) IR (cm$^{-1}$): 1215 ($SO_2$), 1348 ($SO_2$) Elemental analysis: found: C, 20.95%; H, 1.05%; N, 2.08%. calculated: C, 21.04%; H, 0.88%; N, 2.04%.

EXAMPLE 3

Production of (fluoroalkyl)(fluorophenyl)iodonium imide

Compound 3

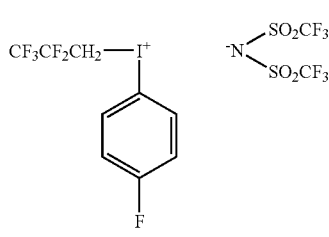

(Compound 3)

Compound 3 was obtained in the same manner as in Example 1, except for the use of $CF_3CF_2CH_2I(OCOCF_3)_2$ (4.86 g, 10 mmol), fluorobenzene (1.41 ml, 15 mmol), and $HN(SO_2CF_3)_2$ (2.81 g, 10 mmol) as starting materials and $CClF_2CCl_2F$ (20 ml) as a solvent (yield 72%).

Melting point: 91.0-93.0° C. $^1$H-NMR (in $CD_3CN$, ppm): δ 8.17 (dd, J=9, 4 Hz, o-H), 7.36 (t, J=9 Hz, m-H), 4.78 (t, J=17 Hz, $CH_2$) $^{19}$F-NMR (internal standard: $C_6F_6$, in $CD_3CN$, ppm): δ 84.1 (s, $CF_3S$), 80.3 (s, $CF_3$), 60.0 (m, p-F), 55.5 (t, J=17 Hz, $CF_2$) IR (cm$^{-1}$): 1199 ($SO_2$), 1346 ($SO_2$) Elemental analysis: found: C, 20.63%; H, 1.08%; N, 2.26%. calculated: C, 20.80%; H, 0.95%; N, 2.21%.

EXAMPLE 4

Production of (fluoroalkyl)(fluorophenyl)iodonium imide

Compound 4

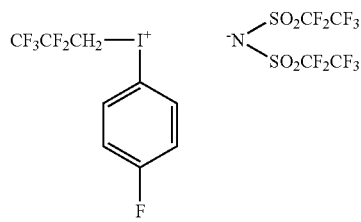
(Compound 4)

Compound 4 was obtained in the same manner as in Example 1, except for the use of $CF_3CF_2CH_2I(OCOCF_3)_2$ (9.72 g, 20 mmol), fluorobenzene (2.85 ml, 30 mmol), and $HN(SO_2CF_2CF_3)_2$ (7.62 g, 20 mmol) as starting materials and $CH_2Cl_2$ (40 ml) as a solvent (yield 62%).

Melting point: 99.3-99.8° C. $^1$H-NMR (in $CD_3CN$, ppm): δ 8.17 (m, o-H), 7.35 (m, m-H), 4.78 (t, J=17 Hz, $CH_2$) $^{19}$F-NMR (internal standard: $C_6F_6$, in $CD_3CN$, ppm): δ 84.5 (s, $CF_3CF_2S$), 80.5 ($CF_3$), 60.1 (m, p-F), 55.8 (t, J=10 Hz, $CF_2$), 46.2 (s, $CF_2S$) IR (cm$^{-1}$): 1221 ($SO_2$), 1349 ($SO_2$) Elemental analysis: found: C, 21.15%; H, 0.97%; N, 2.09%. calculated: C, 21.24%; H, 0.82%; N, 1.91%.

EXAMPLE 5

Production of (fluoroalkyl)(fluorophenyl)iodonium imide

Compound 5

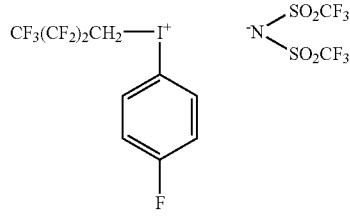
(Compound 5)

Compound 5 was obtained in the same manner as in Example 1, except for the use of $CF_3(CF_2)_2CH_2I(OCOCF_3)_2$ (5.36 g, 10 mmol), fluorobenzene (1.41 ml, 15 mmol), and $HN(SO_2CF_3)_2$ (2.81 g, 10 mmol) as starting materials and $CH_2Cl_2$ (12.5 ml) as a solvent (yield 84%).

Melting point: 58.7-59.7° C. $^1$H-NMR (in $CD_3CN$, ppm): δ 8.19 (dd, J=9, 5 Hz, o-H), 7.35 (t, J=9 Hz m-H), 4.84 (t, J=18 Hz, $CH_2$) $^{19}$F-NMR (internal standard: $C_6F_6$, in $CD_3CN$, ppm): δ 84.4 (s, $SCF_3$), 83.3 (t, J=10 Hz, $CF_3$), 60.2 (m, p-F), 59.0 (m, $CF_2$), 38.2 (m, $CF_2$) IR (cm$^{-1}$): 1338 ($SO_2$), 1203 ($SO_2$) Elemental analysis: found: C, 20.82%; H, 0.86%; N, 2.18%.
calculated: C, 21.03%; H, 0.88%; N, 2.04%.

EXAMPLE 6

Production of (fluoroalkyl)(fluorophenyl)iodonium imide

Compound 6

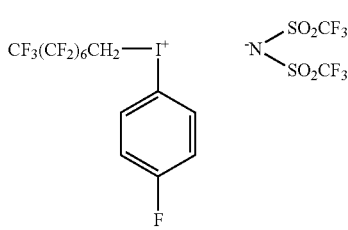
(Compound 6)

Compound 6 was obtained in the same manner as in Example 1, except for the use of $CF_3(CF_2)_6CH_2I(OCOCF_3)_2$ (7.36 g, 10 mmol), fluorobenzene (1.41 ml, 15 mmol), and $HN(SO_2CF_3)_2$ (2.81 g, 10 mmol) as starting materials and $CH_2Cl_2$ (12.5 ml) as a solvent (yield 88%).

Melting point: 67.4-68.0° C. $^1$H-NMR (in $CD_3CN$, ppm): δ 8.20 (dd, J=9, 5 Hz, o-H), 7.35 (t, J=9 Hz, m-H), 4.86 (t, J=18 Hz, $CH_2$) $^{19}$F-NMR (internal standard: $C_6F_6$, in $CD_3CN$, ppm): δ 84.4 (s, $SCF_3$), 82.9 (m, $CF_3$), 60.2 (m, p-F), 60.0 (m, $CF_2$), 42.7 (m, $CF_2$ ×2), 42.1 (m, $CF_2$), 41.3 (m, $CF_2$), 37.9 (m, $CF_2$) IR (cm$^{-1}$): 1354 ($SO_2$), 1204 ($SO_2$) Elemental analysis: found: C, 21.65%; H, 0.69%; N, 2.01%. calculated: C, 21.71%; H, 0.68%; N, 1.58%.

EXAMPLE 7

Production of (fluoroalkyl)(phenyl)iodonium imide compound 7

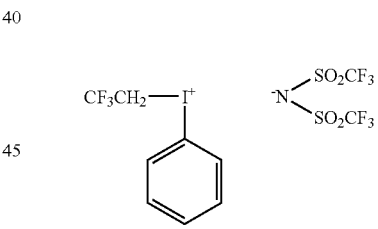
(Compound 7)

Reaction was conducted in the same manner as in Example 1, except for the use of $CF_3CH_2I(OCOCF_3)_2$ (21.8 g, 50 mmol), benzene (6.7 ml, 75 mmol), and $HN(SO_2CF_3)_2$ (14.1 g, 50 mmol) as starting materials and $CH_2Cl_2$ (62.5 ml) as a solvent.

After the completion of the reaction, methylene chloride as a solvent was removed by distillation using an evaporator at room temperature, and trifluoroacetic acid as a side product was then removed by distillation using a vacuum pump. Chloroform was added to the obtained oil product, and the resulting solid product was separated by filtration. This solid product was dissolved in acetonitrile/chloroform, the solution was allowed to stand in a freezer (−20° C.) overnight, and the resulting crystal was separated by filtration. Thus, (2,2,2-trifluoroethyl)(phenyl)iodonium bis(trifluoromethanesulfonyl)imide (compound 7) was obtained (yield: 71%). A sample for analysis was obtained by recrystallization from acetonitrile/chloroform.

Melting point: 76.0-78.0° C. (documented value (Chemical Communication, 1998, pp. 2241-2242): 77-79° C.)
$^1$H-NMR (in CD$_3$CN, ppm): δ 8.13 (d, J=8 Hz, o-H), 7.83 (t, J=8 Hz, p-H), 7.62 (t, J=8 Hz, m-H), 4.76 (q, J=10 Hz, CH$_2$)
$^{19}$F-NMR (internal standard: C$_6$F$_6$, in CD$_3$CN, ppm): δ 101.4 (t, J=10 Hz CF$_3$), 84.2 (s, CF$_3$S) IR (cm$^{-1}$): 1202 (SO$_2$), 1361 (SO$_2$) Elemental analysis: found: C, 21.03%; H, 1.38%; N, 2.51%. calculated: C, 21.18%; H, 1.24%; N, 2.47%.

EXAMPLE 8

Production of (fluoroalkyl)(phenyl)iodonium imide compound 8

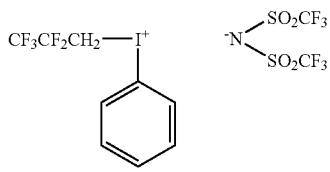

(Compound 8)

Reaction was conducted in the same manner as in Example 1, except for the use of CF$_3$CF$_2$CH$_2$I(OCOCF$_3$)$_2$ (4.86 g, 10 mmol), benzene (1.34 ml, 15 mmol), and HN(SO$_2$CF$_3$)$_2$ (2.81 g, 10 mmol) as starting materials and CH$_2$Cl$_2$ (12.5 ml) as a solvent.

After the completion of the reaction, methylene chloride as a solvent was removed by distillation using an evaporator at room temperature, and trifluoroacetic acid as a side product was then removed by distillation using a vacuum pump. The oil product was dissolved in a minimal amount of acetonitrile, and a large amount of chloroform was added thereto to recover the oil product separated in the lower layer. Thus, (2,2,3,3,3-pentafluoropropyl)(phenyl)iodonium bis(trifluoromethanesulfonyl) imide (compound 8) was obtained (yield: 61%).

$^1$H-NMR (in CD$_3$CN, ppm): δ 8.15 (d, J=8 Hz, o-H), 7.82 (t, J=8 Hz, p-H), 7.61 (t, J=8 Hz, m-H), 4.80 (t, J=17 Hz, CH$_2$)
$^{19}$F-NMR (internal standard: C$_6$F$_6$, in CD$_3$CN, ppm): δ 84.2 (s, CF$_3$S), 80.4 (s, CF$_3$), 55.7(t, J=17 Hz, CF$_2$) IR (cm$^{-1}$): 1201(SO$_2$), 1345(SO$_2$) Elemental analysis: found: C, 19.89%; H, 1.24%; N, 2.07%. calculated: C, 21.41%; H, 1.14%; N, 2.27%.

EXAMPLE 9

Synthesis of 1-methyl-3-(2',2',2'-trifluoroethyl)imidazolium bis(trifluoromethanesulfonyl)imide using compound 7

Compound 9

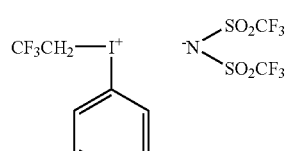

(Compound 7)

+

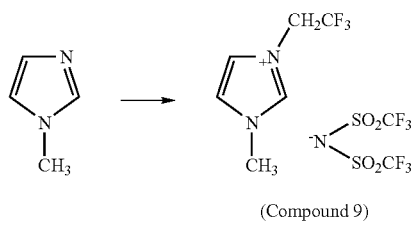

(Compound 9)

(2,2,2-Trifluoroethyl)(phenyl)iodonium bis(trifluoromethanesulfonyl)imide (compound 7) (3.4 g, 6 mmol) and methylene chloride (12 ml) were placed in a reaction vessel to convert the inside of the reaction vessel to a nitrogen atmosphere. While stirring and cooling in an ice bath, 1-methylimidazole (0.49 g, 6 mmol) was added dropwise thereto over the course of 1 minute. After the dropwise addition thereof, the ice bath was removed, and the mixture was allowed to react at room temperature for 3 hours. After the completion of the reaction, the solvent was removed by distillation. The resulting liquid product was washed with water and then with hexane in order to remove a side product, iodobenzene. Subsequently, this liquid product was dissolved in a small amount of ethyl acetate, and a large amount of ether was added thereto to separate the liquid product. The liquid product was separated from the solvent and then dried at 110° C. under reduced pressure using a vacuum pump. Thus, pure 1-methyl-3-(2',2',2'-trifluoroethyl)imidazolium bis(trifluoromethanesulfonyl)imide (compound 9) was obtained as a liquid substance (yield 1.94 g, 73%). When the product is colored, it may be subjected to decolorization with active carbon. Physical property, elemental analysis and spectral data of the compound 9 are shown in Table 8.

EXAMPLE 10

Synthesis of 1-methyl-3-(2',2',2'-trifluoroethyl)imidazolium bis(trifluoromethanesulfonyl)imide and p-fluoroiodobenzene using compound 1

Compound 9

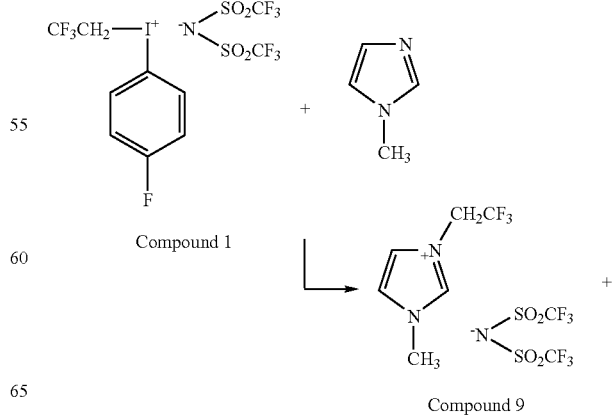

Compound 9

-continued

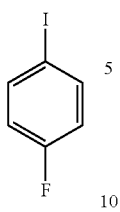

(2,2,2-Trifluoroethyl)(4-fluorophenyl)iodonium bis(trifluoromethanesulfonyl)imide (17.6 g, 30 mmol) and methylene chloride (60 ml) were placed in a reaction vessel to convert the inside of the reaction vessel to a nitrogen atmosphere. While stirring and cooling in an ice bath, 1-methylimidazole (2.46 g, 30 mmol) was added dropwise thereto. After the dropwise addition thereof, the ice bath was removed, and the mixture was allowed to react at room temperature for 3 hours. After the completion of the reaction, the solvent was removed by distillation. The resulting liquid product was washed with hexane (or pentane), water, and then hexane (or pentane). Subsequently, this liquid product was dissolved in a small amount of ethyl acetate, and a large amount of ether was added thereto to separate the liquid product. The liquid product was separated from the solvent and then dried at 110° C. for 6 hours under reduced pressure using a vacuum pump. Thus, pure 1-methyl-3-(2',2',2'-trifluoroethyl)imidazolium bis(trifluoromethanesulfonyl)imide (compound 9) was obtained as a liquid substance (yield 11.5 g, 86%). When the product is colored, it may be subjected to decolorization with active carbon. Separately, p-fluoroiodobenzene was obtained from the aforementioned hexane (or pentane) wash in a substantially quantitative manner.

EXAMPLE 11

Synthesis of 1-methyl-3-(2',2',3',3',3'-pentafluoropropyl)imidazolium bis(trifluoromethanesulfonyl)imide and p-fluoroiodobenzene using compound 3

Compound 11

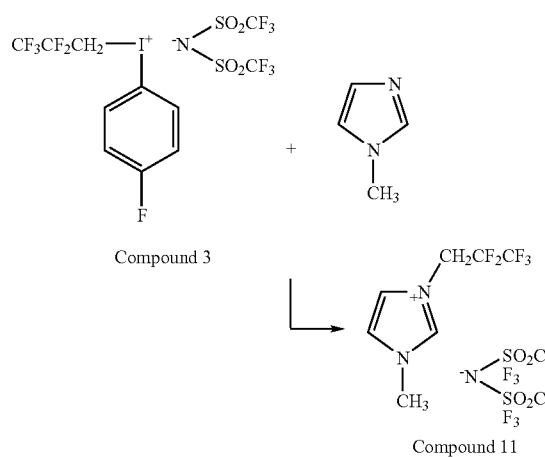

-continued

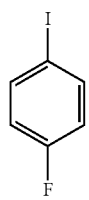

Pure 1-methyl-3-(2',2',3',3',3'-pentafluoropropyl)imidazolium bis-(trifluoromethanesulfonyl)imide (compound 11) was obtained as a liquid substance in the same manner as in Example 10, except that compound 3 was used instead of compound 1 (yield 90%). Also, p-fluoroiodobenzene was obtained in a substantially quantitative manner. Physical property, elemental analysis and spectral data of the compound 11 are shown in Table 8.

EXAMPLE 12

Synthesis of 1-methyl-3-(2',2',2'-trifluoroethyl)imidazolium N-(trifluoromethanesulfonyl)trifluoroacetamide by salt exchange Compound 12

A starting material, 1-methyl-3-(2',2',2'-trifluoroethyl)imidazolium triflate, can be synthesized as shown below.

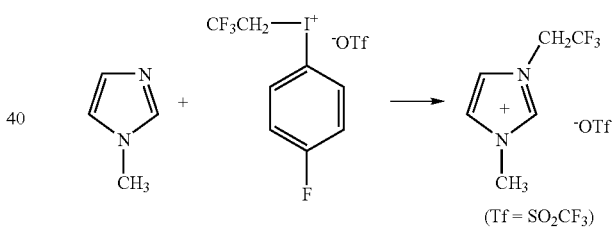

1-Methylimidazole (0.82 g, 10 mmol) was added to methylene chloride (20 ml), and (2,2,2-trifluoroethyl)(phenyl)iodonium triflate (4.54 g, 10 mmol) was added thereto while stirring in an ice bath. Thereafter, the mixture was stirred at room temperature for 3 hours. Methylene chloride was removed by distillation, and the residue was then dried using a vacuum pump while being heated. Thus, 1-methyl-3-(2',2',2'-trifluoroethyl)imidazolium triflate of interest was obtained in a substantially quantitative manner.

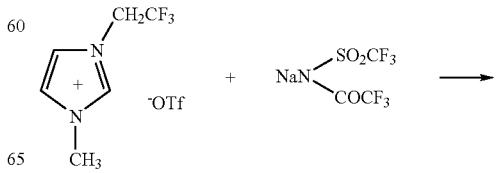

-continued

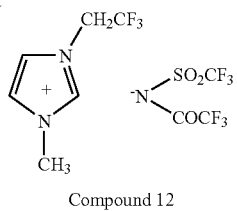

Compound 12

1-Methyl-3-(2',2',2'-trifluoroethyl)imidazolium triflate (10 mmol) and water (10 ml) were placed in a reaction vessel, and a solution of sodium N-(trifluoromethanesulfonyl)trifluoroacetamide (2.94 g, 11 mmol) and water (3 ml) were added thereto while stirring. The mixture was then stirred for 15 minutes. The lower oil layer was separated, and this layer was repeatedly washed with water. The obtained oil product was dehydrated using a vacuum pump at 110° C. for 3 hours, and 1-methyl-3-(2',2',2'-trifluoroethyl)imidazolium N-(trifluoromethanesulfonyl)-trifluoroacetamide (compound 12) was obtained (yield 2.87 g, 70%). When further purification is required, the oil product may be dissolved in a small amount of ethyl acetate, and a large amount of ether may be added thereto to separate the oil product and the product may be dried. Alternatively, when the product is colored, it may be treated with active carbon. Physical property, elemental analysis and spectral data of the compound 12 are shown in Table 8.

EXAMPLES 14 TO 22

A variety of fluoroalkyl-substituted imidazolium salts were synthesized in accordance with process A or process B using starting materials and reaction conditions shown in Table 1. Process A is similar to the method as described in Example 10, and process B is similar to the method as described in Example 12 (salt exchange).

TABLE 1

Synthesis of fluoroalkyl-substituted imidazolium salts

| Ex. | Method | Material 1 | Material 2 | Reaction Conditions | Product | Yield |
|---|---|---|---|---|---|---|
| 14 | A | imidazole 5 mmol | $CF_3CH_2$—$I^+$—$N(SO_2CF_3)_2$ (p-F-phenyl) 10.25 mmol | $CH_2Cl_2$ 20 mL, 0° C. → r.t., 1 h, $Na_2CO_3$ 10 mmol | 1,3-bis($CH_2CF_3$)imidazolium $N(SO_2CF_3)_2$ | 62% |
| 15 | A | imidazole 5 mmol | $CF_3CF_2CH_2$—$I^+$—$N(SO_2CF_3)_2$ (p-F-phenyl) 10.25 mmol | $CH_2Cl_2$ 20 mL, 0° C. → r.t., 3 h, $Na_2CO_3$ 15 mmol | 1,3-bis($CH_2CF_2CF_3$)imidazolium $N(SO_2CF_3)_2$ | 78% |
| 16 | A | 1-($CH_2CF_3$)imidazole 5 mmol | $CF_3CF_2CH_2$—$I^+$—$N(SO_2CF_3)_2$ (p-F-phenyl) 5 mmol | $CH_2Cl_2$ 10 mL, 0° C. → r.t., 2.2 h | 1-($CH_2CF_2CF_3$)-3-($CH_2CF_3$)imidazolium $N(SO_2CF_3)_2$ | 78% |
| 17 | A | 1-methylimidazole 5 mmol | $CF_3CF_2CH_2$—$I^+$—$N(SO_2CF_2F_3)_2$ (p-F-phenyl) 5 mmol | $CH_2Cl_2$ 10 mL, 0° C. → r.t., 1.5 h | 1-($CH_2CF_2CF_3$)-3-methylimidazolium $N(SO_2CF_2CF_3)_2$ | 80% |
| 18 | A | 1-methylimidazole 5 mmol | $CF_3CH_2$—$I^+$—$N(SO_2CF_2CF_3)_2$ (p-F-phenyl) 5 mmol | $CH_2Cl_2$ 10 mL, 0° C. → r.t., 1.5 h | 1-($CH_2CF_3$)-3-methylimidazolium $N(SO_2CF2CF_3)_2$ | 80% |

TABLE 1-continued

Synthesis of fluoroalkyl-substituted imidazolium salts

| Ex. | Method | Material 1 | Material 2 | Reaction Conditions | Product | Yield |
|---|---|---|---|---|---|---|
| 19 | B | 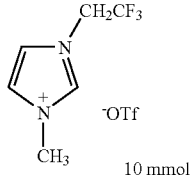 10 mmol | 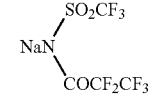 11 mmol | $H_2O$ 10 mL r.t., 5 min | 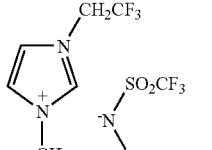 | 85% |
| 20 | B | 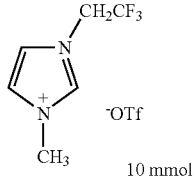 10 mmol | 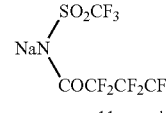 11 mmol | $H_2O$ 10 mL r.t., 20 min | 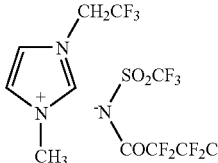 | 89% |
| 21 | B | 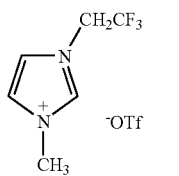 10 mmol | 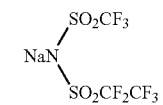 10.5 mmol | $H_2O$ 10 mL r.t., 10 min | 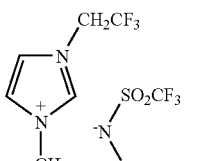 | 86% |
| 22 | B | 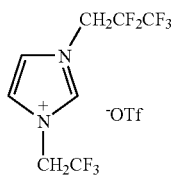 5 mmol | 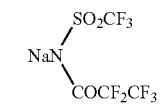 5.5 mmol | $H_2O$ 5 mL 80° C., 10 min | 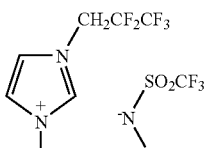 | 74% |

EXAMPLES 23 TO 30

A variety of fluoroalkyl-substituted pyridinium salts were synthesized in accordance with process A or process B using starting materials and reaction conditions shown in Table 2. Process A is similar to the method as described in Example 10, and process B is similar to the method as described in Example 12 (salt exchange).

TABLE 2

Synthesis of fluoroalkyl-substituted pyridinium salts

| Ex. | Method | Material 1 | Material 2 | Reaction Conditions | Product | Yield |
|---|---|---|---|---|---|---|
| 23 | A | 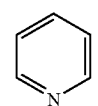 5.25 mmol | 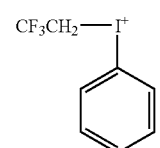 5 mmol | $CH_2Cl_2$ 10 mL 0° C. → r.t., 30 min | 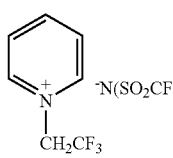 | 89% |

TABLE 2-continued

Synthesis of fluoroalkyl-substituted pyridinium salts

| Ex. | Method | Material 1 | Material 2 | Reaction Conditions | Product | Yield |
|---|---|---|---|---|---|---|
| 24 | A | pyridine, 5.25 mmol | CF₃CF₂CH₂—I⁺(4-F-C₆H₄) ⁻N(SO₂CF₃)₂, 5 mmol | CH₂Cl₂ 10 mL, 0° C. → r.t., 1 h | 1-(CH₂CF₂CF₃)-pyridinium ⁻N(SO₂CF₃)₂ | 89% |
| 25 | A | 3-methylpyridine, 5.25 mmol | CF₃CH₂—I⁺(4-F-C₆H₄) ⁻N(SO₂CF₃)₂, 5 mmol | CH₂Cl₂ 10 mL, 0° C. → r.t., 2.75 h | 3-methyl-1-(CH₂CF₃)-pyridinium ⁻N(SO₂CF₃)₂ | 88% |
| 26 | A | 3-methylpyridine, 5.25 mmol | CF₃CF₂CH₂—I⁺(4-F-C₆H₄) ⁻N(SO₂CF₃)₂, 5 mmol | CH₂Cl₂ 10 mL, 0° C. → r.t., 2.75 h | 3-methyl-1-(CH₂CF₂CF₃)-pyridinium ⁻N(SO₂CF₃)₂ | 64% |
| 27 | A | 3-ethylpyridine, 42 mmol | CF₃CH₂—I⁺(4-F-C₆H₄) ⁻N(SO₂CF₃)₂, 40 mmol | CH₂Cl₂ 50 mL, 0° C. → r.t., 3.1 h | 3-ethyl-1-(CH₂CF₃)-pyridinium ⁻N(SO₂CF₃)₂ | 62% |
| 28 | A | 3-methoxypyridine, 10 mmol | CF₃CH₂—I⁺(4-F-C₆H₄) ⁻N(SO₂CF₃)₂, 10.5 mmol | CH₂Cl₂ 20 mL, 0° C. → r.t., 3.1 h | 3-methoxy-1-(CH₂CF₃)-pyridinium ⁻N(SO₂CF₃)₂ | 82% |
| 29 | B | 3-ethyl-1-(CH₂CF₃)-pyridinium ⁻OTf, 10 mmol | NaN(SO₂CF₃)(COCF₃), 11 mmol | H₂O 20 mL, r.t., 10 min | 3-ethyl-1-(CH₂CF₃)-pyridinium ⁻N(SO₂CF₃)(COCF₃) | 82% |
| 30 | B | 3-ethyl-1-(CH₂CF₃)-pyridinium ⁻OTf, 10 mmol | NaN(SO₂CF₃)(COCF₂CF₃), 11 mmol | H₂O 20 mL, r.t., 10 min | 3-ethyl-1-(CH₂CF₃)-pyridinium ⁻N(SO₂CF₃)(COCF₂CF₃) | 86% |

EXAMPLES 31 TO 34

A variety of fluoroalkoxy-substituted pyridinium salts were synthesized in accordance with process A or process B using starting materials and reaction conditions shown in Table 3. Process A is similar to the method as described in Example 10, and process B is similar to the method as described in Example 12 (salt exchange).

TABLE 3

Synthesis of fluoroalkyloxy-substituted pyridinium salts

| Ex. | Method | Material 1 | Material 2 | Reaction Conditions | Product | Yield |
|---|---|---|---|---|---|---|
| 31 | A | pyridine N-oxide, 40 mmol | CF$_3$CH$_2$—I$^+$—C$_6$H$_4$F  $^-$N(SO$_2$CF$_3$)$_2$, 42 mmol | CH$_2$Cl$_2$ 50 mL, 0° C. → r.t., 3 h | N-(OCH$_2$CF$_3$)pyridinium $^-$N(SO$_2$CF$_3$)$_2$ | 85% |
| 32 | A | 3-methylpyridine N-oxide, 30 mmol | CF$_3$CH$_2$—I$^+$—C$_6$H$_4$F  $^-$N(SO$_2$CF$_3$)$_2$, 31.5 mmol | CH$_2$Cl$_2$ 50 mL, 0° C. → r.t., 3 h | 3-methyl-N-(OCH$_2$CF$_3$)pyridinium $^-$N(SO$_2$CF$_3$)$_2$ | 84% |
| 33 | B | N-(OCH$_2$CF$_3$)pyridinium $^-$OTf, 10 mmol | NaN(SO$_2$CF$_3$)(COCF$_3$), 11 mmol | H$_2$O 10 mL, r.t., 5 min | N-(OCH$_2$CF$_3$)pyridinium $^-$N(SO$_2$CF$_3$)(COCF$_3$) | 57% |
| 34 | B | N-(OCH$_2$CF$_3$)pyridinium $^-$OTf, 10 mmol | NaN(SO$_2$CF$_3$)(COCF$_2$CF$_3$), 11 mmol | H$_2$O 10 mL, r.t., 10 min | N-(OCH$_2$CF$_3$)pyridinium $^-$N(SO$_2$CF$_3$)(COCF$_2$CF$_3$) | 79% |

EXAMPLES 35 TO 61

A variety of fluoroalkyl-substituted ammonium salts were synthesized in accordance with process A or process B using starting materials and reaction conditions shown in Table 4. Process A is similar to the method as described in Example 10, and process B is similar to the method as described in Example 12 (salt exchange).

TABLE 4

Synthesis of fluoroalkyl-substituted ammonium salts

| Ex. | Method | Material 1 | Material 2 | Reaction Conditions | Product | Yield |
|---|---|---|---|---|---|---|
| 35 | A | (CH$_3$CH$_2$)$_3$N, 10 mmol | CF$_3$CH$_2$—I$^+$—C$_6$H$_4$F  $^-$N(SO$_2$CF$_3$)$_2$, 10.5 mmol | CH$_2$Cl$_2$/H$_2$O(1/1) 40 mL, r.t., 1 h | (CH$_3$CH$_2$)$_3$NCH$_2$CF$_3$$^+$  $^-$N(SO$_2$CF$_3$)$_2$ | 67% |

TABLE 4-continued

Synthesis of fluoroalkyl-substituted ammonium salts

| Ex. | Method | Material 1 | Material 2 | Reaction Conditions | Product | Yield |
|---|---|---|---|---|---|---|
| 36 | A | $CH_3(CH_2)_2CH_2N(CH_2CH_3)_2$<br>10 mmol | $CF_3CH_2-I^+\ ^-N(SO_2CF_3)_2$<br>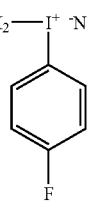<br>11 mmol | $CH_2Cl_2/H_2O(1/1)$ 40 mL<br>r.t., 1 h | $CH_3(CH_2)_2CH_2\overset{+}{N}(CH_2CH_3)_2$<br>$\mid$<br>$CH_2CF_3$<br><br>$^-N(SO_2CF_3)_2$ | 67% |
| 37 | A | $CH_3(CH_2)_2CH_2N(CH_3)_2$<br>40 mmol | $CF_3CH_2-I^+\ ^-N(SO_2CF_3)_2$<br>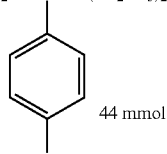<br>44 mmol | $CH_2Cl_2/H_2O(2/1)$ 120 mL<br>r.t., 1.8 h | $CH_3(CH_2)_2CH_2\overset{+}{N}(CH_3)_2$<br>$\mid$<br>$CH_2CF_3$<br><br>$^-N(SO_2CF_3)_2$ | 91% |
| 38 | B | $CH_3(CH_2)_2CH_2\overset{+}{N}(CH_3)_2$<br>$\mid$<br>$^-OTf\ \ CH_2CF_3$<br>18.8 mmol | $LiN(SO_2CF_3)_2$<br>18.8 mmol | $H_2O$ 30 mL<br>r.t., 5 min | $CH_3(CH_2)_2CH_2\overset{+}{N}(CH_3)_2$<br>$\mid$<br>$CH_2CF_3$<br><br>$^-N(SO_2CF_3)_2$ | 97% |
| 39 | A | $CH_3(CH_2)_4CH_2N(CH_2CH_3)_2$<br>10 mmol | $CF_3CH_2-I^+\ ^-N(SO_2CF_3)_2$<br>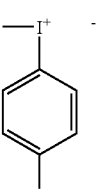<br>11 mmol | $CH_2Cl_2/H_2O(1/1)$ 40 mL<br>$CF_3CH_2OH$ 50 mmol<br>0° C. → r.t., 1.5 h | $CH_3(CH_2)_4CH_2\overset{+}{N}(CH_2CH_3)_2$<br>$\mid$<br>$CH_2CF_3$<br><br>$^-N(SO_2CF_3)_2$ | 77% |
| 40 | A | 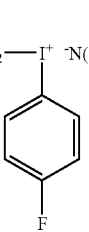<br>2 mmol | $CF_3CH_2-I^+\ ^-N(SO_2CF_3)_2$<br>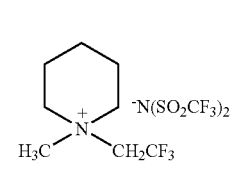<br>2.2 mmol | $CH_2Cl_2/H_2O(1/1)$ 8 mL<br>$CF_3CH_2OH$ 10 mmol<br>0° C. → r.t., 3.1 h | 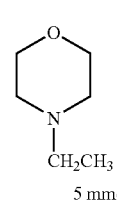 | 63% |
| 41 | A | 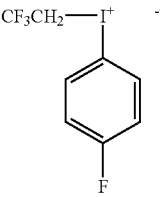<br>5 mmol | $CF_3CH_2-I^+\ ^-N(SO_2CF_3)_2$<br>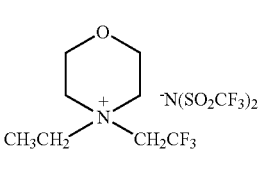<br>5.5 mmol | $CH_2Cl_2/H_2O(1/1)$ 20 mL<br>$CF_3CH_2OH$ 2.5 mmol<br>0° C. → r.t., 2.5 h | 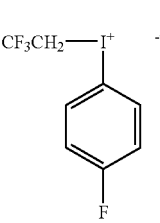 | 65% |
| 42 | A | $CH_3(CH_2)_4CH_2NHCH_3$<br>10 mmol | $CF_3CH_2-I^+\ ^-N(SO_2CF_3)_2$<br><br>23 mmol | $CH_2Cl_2/H_2O(1/1)$ 40 mL<br>$NaHCO_3$ 15 mmol<br>r.t., 5 h | $CH_3(CH_2)_4CH_2\overset{+}{N}(CH_2CF_3)_2$<br>$\mid$<br>$CH_3$<br><br>$^-N(SO_2CF_3)_2$ | 95% |

TABLE 4-continued

Synthesis of fluoroalkyl-substituted ammonium salts

| Ex. | Method | Material 1 | Material 2 | Reaction Conditions | Product | Yield |
|---|---|---|---|---|---|---|
| 43 | A | $CH_3(CH_2)_2CH_2NHCH_3$<br>10 mmol | $CF_3CH_2-I^+-C_6H_4F$ $^-N(SO_2CF_3)_2$<br>23 mmol | $CH_2Cl_2/H_2O(1/1)$ 40 mL<br>$NaHCO_3$ 15 mmol<br>0° C. ⟶ r.t., 5 h | $CH_3(CH_2)_2CH_2\overset{+}{N}(CH_2CF_3)_2$<br>$\mid$<br>$CH_3$<br>$^-N(SO_2CF_3)_2$ | 67% |
| 44 | B | $CH_3(CH_2)_2CH_2\overset{+}{N}(CH_3)_2$<br>$\mid$<br>$^-OTf$  $CH_2CF_3$<br>10 mmol | $NaN(SO_2CF_3)(COCF_3)$<br>11 mmol | $H_2O$ 20 mL<br>r.t., 10 min | $CH_3(CH_2)_2CH_2\overset{+}{N}(CH_3)_2$<br>$\mid$<br>$CH_2CF_3$<br>$^-N(SO_2CF_3)(COCF_3)$ | 76% |
| 45 | B | $CH_3(CH_2)_2CH_2\overset{+}{N}(CH_3)_2$<br>$\mid$<br>$^-OTf$  $CH_2CF_3$<br>10 mmol | $NaN(SO_2CF_3)(COCF_2CF_3)$<br>11 mmol | $H_2O$ 20 mL<br>r.t., 20 min | $CH_3(CH_2)_2CH_2\overset{+}{N}(CH_3)_2$<br>$\mid$<br>$CH_2CF_3$<br>$^-N(SO_2CF_3)(COCF_2CF_3)$ | 86% |
| 46 | B | $CH_3(CH_2)_4CH_2\overset{+}{N}(CH_2CF_3)_2$<br>$\mid$<br>$^-OTf$  $CH_3$<br>10 mmol | $NaN(SO_2CF_3)(COCF_3)$<br>11 mmol | $CH_3OH/H_2O(11/30)$ 41 mL<br>r.t., 11 min | $CH_3(CH_2)_4CH_2\overset{+}{N}(CH_2CF_3)_2$<br>$\mid$<br>$CH_3$<br>$^-N(SO_2CF_3)(COCF_3)$ | 74% |
| 47 | B | $CH_3(CH_2)_4CH_2\overset{+}{N}(CH_2CF_3)_2$<br>$\mid$<br>$^-OTf$  $CH_3$<br>10 mmol | $NaN(SO_2CF_3)(COCF_2CF_3)$<br>11 mmol | $CH_3OH/H_2O(9/30)$ 39 mL<br>r.t., 11 min | $CH_3(CH_2)_4CH_2\overset{+}{N}(CH_2CF_3)_2$<br>$\mid$<br>$CH_3$<br>$^-N(SO_2CF_3)(COCF_2CF_3)$ | 67% |
| 48 | A | $(CH_3CH_2OCH_2CH_2)_2NH$<br>5 mmol | $CF_3CH_2-I^+-C_6H_4F$ $^-N(SO_2CF_3)_2$<br>11 mmol | $CH_2Cl_2/H_2O(1/1)$ 20 mL<br>$NaHCO_3$ 6 mmol<br>0° C. ⟶ r.t., 14 h | $(CH_3CH_2OCH_2CH_2)_2\overset{+}{N}(CH_2CF_3)_2$<br>$^-N(SO_2CF_3)_2$ | 81% |
| 49 | A | $CH_3OCH_2CH_2NHCH_2CH_3$<br>5 mmol | $CF_3CH_2-I^+-C_6H_4F$ $^-N(SO_2CF_3)_2$<br>11 mmol | $CH_2Cl_2/H_2O(1/1)$ 20 mL<br>$NaHCO_3$ 6 mmol<br>0° C. ⟶ r.t., 17 h | $CH_3OCH_2CH_2\overset{+}{N}(CH_2CF_3)_2$<br>$\mid$<br>$CH_2CH_3$<br>$^-N(SO_2CF_3)_2$ | 80% |

TABLE 4-continued

Synthesis of fluoroalkyl-substituted ammonium salts

| Ex. | Method | Material 1 | Material 2 | Reaction Conditions | Product | Yield |
|---|---|---|---|---|---|---|
| 50 | A | $CH_3CH_2OCH_2CH_2N(CH_2CH_3)_2$<br>10 mmol | $CF_3CH_2-I^+$-(4-F-C$_6$H$_4$) $^-N(SO_2CF_3)_2$<br>10.5 mmol | $CH_2Cl_2/H_2O(2/1)$ 30 mL<br>0° C. → r.t., 3 h | $CH_3CH_2OCH_2CH_2\overset{+}{N}(CH_2CH_3)_2$<br>\|<br>$CH_2CF_3$<br><br>$^-N(SO_2CF_3)_2$ | 89% |
| 51 | B | $CH_3(CH_2)_2CH_2\overset{+}{N}(CH_3)_2$<br>\|<br>$CH_2CF_3$<br>$^-OTf$<br>10 mmol | $NaN\begin{smallmatrix}SO_2CF_3\\COCF_2CF_2CF_3\end{smallmatrix}$<br>11 mmol | $H_2O$ 20 mL<br>r.t., 10 min | $CH_3(CH_2)_2CH_2\overset{+}{N}(CH_3)_2$<br>\|<br>$CH_2CF_3$<br>$^-N\begin{smallmatrix}SO_2CF_3\\COCF_2CF_2CF_3\end{smallmatrix}$ | 90% |
| 52 | A | $CH_3OCH_2CH_2N(CH_2CH_3)_2$<br>10 mmol | $CF_3CH_2-I^+$-(4-F-C$_6$H$_4$) $^-N(SO_2CF_3)_2$<br>10.5 mmol | $CH_2Cl_2/H_2O(2/1)$ 30 mL<br>0° C. → r.t., 3 h | $CH_3OCH_2CH_2\overset{+}{N}(CH_2CH_3)_2$<br>\|<br>$CH_2CF_3$<br><br>$^-N(SO_2CF_3)_2$ | 84% |
| 53 | B | $CH_3CH_2OCH_2CH_2\overset{+}{N}(CH_2CH_3)_2$<br>\|<br>$CH_2CF_3$<br>$^-OTf$<br>10 mmol | $NaN\begin{smallmatrix}SO_2CF_3\\COCF_2CF_3\end{smallmatrix}$<br>11 mmol | $H_2O$ 10 mL<br>r.t., 15 min | $CH_3CH_2OCH_2CH_2\overset{+}{N}(CH_2CH_3)_2$<br>\|<br>$CH_2CF_3$<br>$^-N\begin{smallmatrix}SO_2CF_3\\COCF_2CF_3\end{smallmatrix}$ | 72% |
| 54 | A | $CH_3CH_2OCH_2CH_2N(CH_3)_2$<br>10 mmol | $CF_3CH_2-I^+$-(4-F-C$_6$H$_4$) $^-N(SO_2CF_3)_2$<br>10.5 mmol | $CH_2Cl_2/H_2O(2/1)$ 30 mL<br>0° C. → r.t., 3 h | $CH_3CH_2OCH_2CH_2\overset{+}{N}(CH_3)_2$<br>\|<br>$CH_2CF_3$<br><br>$^-N(SO_2CF_3)_2$ | 78% |
| 55 | A | $CH_3OCH_2CH_2N(CH_3)_2$<br>10 mmol | $CF_3CH_2-I^+$-(4-F-C$_6$H$_4$) $^-N(SO_2CF_3)_2$<br>10.5 mmol | $CH_2Cl_2/H_2O(2/1)$ 30 mL<br>0° C. → r.t., 3 h | $CH_3OCH_2CH_2\overset{+}{N}(CH_3)_2$<br>\|<br>$CH_2CF_3$<br><br>$^-N(SO_2CF_3)_2$ | 77% |
| 56 | A | $CF_3CH_2OCH_2CH_2N(CH_2CH_3)_2$<br>10 mmol | $CF_3CH_2-I^+$-(4-F-C$_6$H$_4$) $^-N(SO_2CF_3)_2$<br>10.5 mmol | $CH_2Cl_2/H_2O(2/1)$ 30 mL<br>0° C. → r.t., 3 h | $CF_3CH_2OCH_2CH_2\overset{+}{N}(CH_2CH_3)_2$<br>\|<br>$CH_2CF_3$<br><br>$^-N(SO_2CF_3)_2$ | 84% |

TABLE 4-continued

Synthesis of fluoroalkyl-substituted ammonium salts

| Ex. | Method | Material 1 | Material 2 | Reaction Conditions | Product | Yield |
|---|---|---|---|---|---|---|
| 57 | B | $CH_3OCH_2CH_2\overset{+}{N}(CH_3)_2$ | $NaN\begin{smallmatrix}SO_2CF_3\\COCF_2CF_3\end{smallmatrix}$ | $H_2O$ 10 mL r.t., 5 min | $CH_3OCH_2CH_2\overset{+}{N}(CH_3)_2$ | 77% |
|  |  | $\mid$ |  |  | $\mid$ |  |
|  |  | $CH_2CF_3$ |  |  | $CH_2CF_3$ |  |
|  |  | $^-OTf$ |  |  | $^-N\begin{smallmatrix}SO_2CF_3\\COCF_2CF_3\end{smallmatrix}$ |  |
|  |  | 10 mmol | 11 mmol |  |  |  |
| 58 | B | $CH_3CH_2OCH_2CH_2\overset{+}{N}(CH_3)_2$ | $NaN\begin{smallmatrix}SO_2CF_3\\COCF_2CF_3\end{smallmatrix}$ | $H_2O$ 10 mL r.t., 5 min | $CH_3CH_2OCH_2CH_2\overset{+}{N}(CH_3)_2$ | 68% |
|  |  | $\mid$ |  |  | $\mid$ |  |
|  |  | $CH_2CF_3$ |  |  | $CH_2CF_3$ |  |
|  |  | $^-OTf$ |  |  | $^-N\begin{smallmatrix}SO_2CF_3\\COCF_2CF_3\end{smallmatrix}$ |  |
|  |  | 10 mmol | 11 mmol |  |  |  |
| 59 | A | $CH_3CH_2OCH_2CH_2CH_2N(CH_3)_2$ 10 mmol | $CF_3CH_2-I^+-C_6H_4F$ $^-N(SO_2CF_3)_2$ 10.5 mmol | $CH_2Cl_2/H_2O(2/1)$ 30 mL $0°C. \longrightarrow$ r.t., 3 h | $CH_3CH_2OCH_2CH_2CH_2\overset{+}{N}(CH_3)_2$ $\mid$ $CH_2CF_3$ $^-N(SO_2CF_3)_2$ | 72% |
| 60 | A | $CH_3OCH_2CH_2OCH_2CH_2N(CH_3)_2$ 10 mmol | $CF_3CH_2-I^+-C_6H_4F$ $^-N(SO_2CF_3)_2$ 10.5 mmol | $CH_2Cl_2/H_2O(2/1)$ 30 mL $0°C. \longrightarrow$ r.t., 3 h | $CH_3OCH_2CH_2OCH_2CH_2\overset{+}{N}(CH_3)_2$ $\mid$ $^-N(SO_2CF_3)_2 \quad CH_2CF_3$ | 81% |
| 61 | B | $CH_3OCH_2CH_2OCH_2CH_2\overset{+}{N}(CH_3)_2$ $\mid$ $CH_2CF_3$ $^-OTf$ 10 mmol | $NaN\begin{smallmatrix}SO_2CF_3\\COCF_2CF_3\end{smallmatrix}$ 10.5 mmol | $H_2O$ 10 mL r.t., 10 min | $CH_3OCH_2CH_2OCH_2CH_2\overset{+}{N}(CH_3)_2$ $\mid$ $CH_2CF_3$ $^-N\begin{smallmatrix}SO_2CF_3\\COCF_2CF_3\end{smallmatrix}$ | 71% |

EXAMPLES 62 TO 64

A variety of fluoroalkoxy-substituted ammonium salts were synthesized in accordance with process A or process B using starting materials and reaction conditions shown in Table 5. Process A is similar to the method as described in Example 10, and process B is similar to the method as described in Example 12 (salt exchange). In Examples 62, 63, and 64, $(CH_3)_3N^+CH_2CF_3$ $N^-(SO_2CF_3)_2$, $(CH_3CH_2)_3N^+CH_2CF_3$ $N^-(SO_2CF_3)_2$, and $CH_3CH_2CH_2CH_2N^+(CH_3)_2(CH_2CF_3)$ $N^-(SO_2CF_3)_2$ were obtained as side products at yields of 44%, 9%, and 30%, respectively.

TABLE 5

Synthesis of fluoroalkyloxy-substituted ammonium salts

| Ex. | Method | Material 1 | Material 2 | Reaction Conditions | Product | Yield |
|---|---|---|---|---|---|---|
| 62 | A | $(CH_3)_3N \rightarrow O$<br>10 mmol | $CF_3CH_2\text{—}I^+\text{—}C_6H_4F$  $^-N(SO_2CF_3)_2$<br>10.5 mmol | $CH_2Cl_2$ 20 mL<br>0° C. $\longrightarrow$ r.t., 3.1 h | $(CH_3)_3\overset{+}{N}\text{—}OCH_2CF_3$<br>$^-N(SO_2CF_3)_2$ | 32% |
| 63 | A | $(CH_3CH_2)_3N \rightarrow O$<br>6.08 mmol | $CF_3CH_2\text{—}I^+\text{—}C_6H_4F$  $^-N(SO_2CF_3)_2$<br>6.38 mmol | $CH_2Cl_2$ 12 mL<br>0° C. $\longrightarrow$ r.t., 3.1 h | $(CH_3CH_2)_3\overset{+}{N}\text{—}OCH_2CF_3$<br>$^-N(SO_2CF_3)_2$ | 57% |
| 64 | A | $CH_3(CH_2)_2CH_2N(CH_3)_2$<br>$\downarrow$<br>$O$<br>40 mmol | $CF_3CH_2\text{—}I^+\text{—}C_6H_4F$  $^-N(SO_2CF_3)_2$<br>44 mmol | $CH_2Cl_2$ 80 mL<br>0° C. $\longrightarrow$ r.t., 3.1 h | $CH_3(CH_2)_2CH_2\overset{+}{N}(CH_3)_2$<br>$\mid$<br>$OCH_2CF_3$<br>$^-N(SO_2CF_3)_2$ | 54% |

EXAMPLES 65 TO 72

A variety of fluoroalkyl-substituted sulfonium salts were synthesized in accordance with process A or process B using starting materials and reaction conditions shown in Table 6. Process A is similar to the method as described in Example 10, and process B is similar to the method as described in Example 12 (salt exchange).

TABLE 6

Synthesis of fluoroalkyl-substituted sulfonium salts

| Ex. | Method | Material 1 | Material 2 | Reaction Conditions | Product | Yield |
|---|---|---|---|---|---|---|
| 65 | A | $(CH_3CH_2)_2S$<br>40 mmol | $CF_3CH_2\text{—}I^+\text{—}C_6H_4F$  $^-N(SO_2CF_3)_2$<br>42 mmol | $CH_2Cl_2$ 50 mL<br>0° C. $\longrightarrow$ r.t., 3.1 h | $(CH_3CH_2)_2\overset{+}{S}CH_2CF_3$<br>$^-N(SO_2CF_3)_2$ | 89% |
| 66 | A | $(CH_3CH_2)_2S$<br>5.25 mmol | $CF_3CF_2CH_2\text{—}I^+\text{—}C_6H_4F$  $^-N(SO_2CF_3)_2$<br>5 mmol | $CH_2Cl_2$ 10 mL<br>r.t., 3 h | $(CH_3CH_2)_2\overset{+}{S}CH_2CF_2CF_3$<br>$^-N(SO_2CF_3)_2$ | 94% |

TABLE 6-continued

Synthesis of fluoroalkyl-substituted sulfonium salts

| Ex. | Method | Material 1 | Material 2 | Reaction Conditions | Product | Yield |
|---|---|---|---|---|---|---|
| 67 | A | $CH_3CH_2SCH_3$ 10 mmol | $CF_3CH_2-I^+$ $^-N(SO_2CF_3)_2$ (4-F-C$_6$H$_4$) 9.5 mmol | $CH_2Cl_2$ 15 mL 0° C. ⟶ r.t., 3.1 h | $CH_3CH_2\overset{+}{S}CH_3$ $|$ $CH_2CF_3$ $^-N(SO_2CF_3)_2$ | 88% |
| 68 | A | $[CH_3(CH_2)_4CH_2]_2S$ 10 mmol | $CF_3CH_2-I^+$ $^-N(SO_2CF_3)_2$ (4-F-C$_6$H$_4$) 10.5 mmol | $CH_2Cl_2$ 50 mL 0° C. ⟶ r.t., 3.1 h | $[CH_3(CH_2)_4CH_2]_2\overset{+}{S}CH_2CF_3$ $^-N(SO_2CF_3)_2$ | 89% |
| 69 | A | $CH_3CH_2SH$ 5 mmol | $CF_3CH_2-I^+$ $^-N(SO_2CF_3)_2$ (4-F-C$_6$H$_4$) 10.5 mmol | $CH_2Cl_2$ 10 mL $Na_2CO_3$ 15 mmol 0° C. ⟶ r.t., 3.1 h | $CH_3CH_2\overset{+}{S}(CH_2CF_3)_2$ $^-N(SO_2CF_3)_2$ | 32% |
| 70 | A | $CH_3(CH_2)_4CH_2SH$ 10 mmol | $CF_3CH_2-I^+$ $^-N(SO_2CF_3)_2$ (4-F-C$_6$H$_4$) 23 mmol | $CH_2Cl_2/H_2O(1/1)$ 40 mL $NaHCO_3$ 15 mmol 0° C. ⟶ r.t., 3.1 h | $CH_3(CH_2)_4CH_2\overset{+}{S}(CH_2CF_3)_2$ $^-N(SO_2CF_3)_2$ | 72% |
| 71 | B | $(CH_3CH_2)_2\overset{+}{S}CH_2CF_3$ $^-OTf$ 10 mmol | $NaN(SO_2CF_3)(COCF_3)$ 10.5 mmol | $H_2O$ 10 mL r.t., 10 min | $(CH_3CH_2)_2\overset{+}{S}CH_2CF_3$ $^-N(SO_2CF_3)(COCF_3)$ | 69% |
| 72 | B | $(CH_3CH_2)_2\overset{+}{S}CH_2CF_3$ $^-OTf$ 10 mmol | $NaN(SO_2CF_3)(COCF_2CF_3)$ 10.5 mmol | $H_2O$ 10 mL r.t., 10 min | $(CH_3CH_2)_2\overset{+}{S}CH_2CF_3$ $^-N(SO_2CF_3)(COCF_2CF_3)$ | 79% |

EXAMPLES 73 TO 75

A variety of fluoroalkyl-substituted oxazolium, thiazolium, and isoxazolium salts were synthesized in accordance with process A or process B using starting materials and reaction conditions shown in Table 7. Process A is similar to the method as described in Example 10, and process B is similar to the method as described in Example 12 (salt exchange).

TABLE 7

Synthesis of fluoroalkyl-substituted oxazolium, isooxazolium, and thiazolium salts

| Ex. | Method | Material 1 | Material 2 | Reaction Conditions | Product | Yield |
|---|---|---|---|---|---|---|
| 73 | A | oxazole, 10 mmol | $CF_3CH_2-I^+-C_6H_4F$ $^-N(SO_2CF_3)_2$, 10.5 mmol | $CH_2Cl_2$ 20 mL, 0°C → r.t., 3.1 h | N-($CH_2CF_3$)-oxazolium $^-N(SO_2CF_3)_2$ | 37% |
| 74 | A | thiazole, 10 mmol | $CF_3CH_2-I^+-C_6H_4F$ $^-N(SO_2CF_3)_2$, 10.5 mmol | $CH_2Cl_2$ 20 mL, 0°C → r.t., 3.1 h | N-($CH_2CF_3$)-thiazolium $^-N(SO_2CF_3)_2$ | 71% |
| 75 | A | isoxazole, 10 mmol | $CF_3CH_2-I^+-C_6H_4F$ $^-N(SO_2CF_3)_2$, 10.5 mmol | $CH_2Cl_2$ 20 mL, 0°C → r.t., 22.1 h | N-($CH_2CF_3$)-isoxazolium $^-N(SO_2CF_3)_2$ | 58% |

The melting points, elemental analyses, and $^{19}$F-NMR spectral data of compounds obtained in Examples 9 to 75 are shown in Table 8 below. The compounds of a melting point which is room temperature (about 25° C.) or lower showed a liquid state at room temperature. The compound of a melting point which is higher than room temperature showed or may show a liquid state at room temperature due to the supercooling phenomenon.

TABLE 8

Properties, elemental analyses, and spectral data of the products.

| Ex. | m.p. | Elemental Analysis | $^{19}$F-NMR (in acetonitrile-$d_3$; standard $C_6F_6$) |
|---|---|---|---|
| 9, 10 | <r.t. | Found: C, 21.49; H, 1.85; N, 9.35<br>Calcd: C, 21.58; H, 1.81; N, 9.44 | 91.90(t, J=9.2Hz, $CF_3$), 84.23(s, $SCF_3$) |
| 11 | <r.t. | Found: C, 21.75; H, 1.73; N, 8.41<br>Calcd: C, 21.82; H, 1.63; N, 8.48 | 84.23(s, $SCF_3$), 79.79(s, $CF_3$), 42.59(t, J=15.2Hz, $CF_2$) |
| 12 | <r.t. | Found: C, 26.39; H, 1.96; N, 10.21<br>Calcd: C, 26.41; H, 1.97; N, 10.27 | 91.92(t, J=8.4Hz, 3F, $CF_3$), 87.89(s, 3F, $COCF_3$), 84.55(s, 3F, $SCF_3$) |
| 14 | 63.7-64.9 | Found: C, 21.04; H, 1.43; N, 8.17<br>Calcd: C, 21.06; H, 1.37; N, 8.19 | 92.23(s, 6F, $CF_3$), 84.29(s, 6F, $SCF_3$) |
| 15 | 78.8-79.6 | Found: C, 21.60; H, 1.20; N, 6.94<br>Calcd: C, 21.54; H, 1.15; N, 6.85 | 84.27(s, 6F, $SCF_3$), 79.92(s, 6F, $CF_3$), 42.86(t, J=14.9Hz, $CF_2$) |
| 16 | 48.0(DSC)* | Found: C, 21.35; H, 1.32; N, 7.52<br>Calcd: C, 21.32; H, 1.25; N, 7.46 | 92.19(t, J=8.5Hz, 3F, $CF_3$), 84.25(s, 6F, $SCF_3$), 79.89(s, 3F, $CF_2CF_3$), 42.84(t, J=14.9Hz, 2F, $CF_2$) |
| 17 | 27.0(DSC)* | Found: C, 22.19; H, 1.35; N, 7.05<br>Calcd: C, 22.19; H, 1.35; N, 7.06 | 84.60(s, 6F, $SCF_2CF_3$), 79.83(s, 3F, $CF_3$), 46.20(s, 4F, $SCF_2$), 42.61(t, J=15.4Hz, 2F, $CF_2$) |
| 18 | <r.t. | Calcd: C, 22.03; H, 1.48; N, 7.71<br>Found: C, 21.99; H, 1.53; N, 7.65 | 92.07(t, J=8.5Hz, 3F, $CF_3$), 84.77(s, 6F, $CF_2CF_3$), 46.32(s, 4F, $CF_2$) |
| 19 | <r.t. | Found: C, 26.22; H, 1.78; N, 9.18<br>Calcd: C, 26.15; H, 1.76; N, 9.15 | 91.90(t, J=8.4Hz, 3F, $CF_3$), 84.54(s, 3F, $SCF_3$), 81.31(s, 3F, $CF_2CF_3$), 43.54(s, 2F, $CF_2$) |
| 20 | <r.t. | Found: C, 25.92; H, 1.71; N, 8.19<br>Calcd: C, 25.94; H, 1.58; N, 8.25 | 91.90(t, J=8.5Hz, 3F, $CH_2CF_3$), 84.59(s, 3F, $SCF_3$), 82.86(t, J=8.6Hz, 3F, $CF_3$), 45.94(q, J=8.3HZ, 2F, $COCF_2$), 37.11(s, 2F, —$COCF_2CF_2$) |
| 21 | <r.t. | Found: C, 21.76; H, 1.69; N, 8.54<br>Calcd: C, 21.82; H, 1.63; N, 8.48 | 91.43(t, J=8.4Hz, 3F, $CH_2CF_3$), 84.66(s, 3F, $SCF_3$), 83.75(s, 3F, $CF_2CF_3$), 45.66(s, 2F, $SCF_2$) |

TABLE 8-continued

Properties, elemental analyses, and spectral data of the products.

| Ex. | m.p. | Elemental Analysis | $^{19}$F-NMR(in acetonitrile-$d_3$; standard $C_6F_6$) |
|---|---|---|---|
| 22 | <r.t. | Found: C, 24.74; H, 1.29; N, 7.29<br>Calcd: C, 24.97; H, 1.22; N, 7.28 | 92.16(t, J=8.5Hz, 3F, $CH_2CF_3$), 84.53(s, 3F, $SCF_3$), 81.30(s, 3F, $COCF_2CF_3$), 79.88(s, 3F, $CH_2CF_2CF_3$), 43.51(s, 2F, $COCF_2$), 42.86(t, J=15.5Hz, 2F, $CH_2CF_2$) |
| 23 | 41.0-41.5 | Found: C, 24.35; H, 1.63; N, 6.42<br>Calcd: C, 24.44; N, 6.33 | 92.61(t, J=7.7Hz, $CF_3$), 84.25(s, $SCF_3$) |
| 24 | 65.2-66.5 | Found: C, 24.36; H, 1.47; N, 5.84<br>Calcd: C, 24.40; H, 1.43; N, 5.69 | 84.24(s, $SCF_3$), 80.15(s, $CF_3$), 42.87(t, J=15.2Hz, $CF_2$) |
| 25 | 24.5(DSC)* | Found: C, 26.19; H, 2.11; N, 6.30<br>Calcd: C, 26.32; H, 1.99; N, 6.14 | 92.68(t, J=7.5Hz, $CF_3$), 84.22(s, $SCF_3$) |
| 26 | 35.7 | Found: C, 26.04; H, 1.88; N, 5.23<br>Calcd: C, 26.09; H, 1.79; N, 5.53 | 84.24(s, $SCF_3$), 80.08(s, $CF_3$), 42.95(t, J=15.4Hz, $CF_2$) |
| 27 | <r.t. | Found: C, 28.11; H, 2.38; N, 5.93<br>Calcd: C, 28.09; H, 2.36; N, 5.96 | 92.73(t, J=7.9Hz, 3F, $CF_3$), 84.30(s, 6F, $SCF_3$) |
| 28 | <r.t. | Found: C, 25.51; H, 2.28; N, 5.94<br>Calcd: C, 25.43; H, 1.92; N, 5.93 | 92.83(t, J=8.1Hz, 3F, $CF_3$), 84.29(s, 6F, $SCF_3$) |
| 29 | <r.t. | Found: C, 33.31; H, 2.47; N, 6.44<br>Calcd: C, 33.19; H, 2.55; N, 6.45 | 92.7(t, J=8.4Hz, 3F, $CF_3$), 87.91(s, 3F, $COCF_3$), 84.56(s, 3F, $SCF_3$) |
| 30 | <r.t. | Found: C, 32.35; H, 2.46; N, 5.85<br>Calcd: C, 32.24; H, 2.29; N, 5.78 | 92.71(t, J=8.6Hz, 3F, $CF_3$), 84.56(s, 3F, $SCF_3$), 81.32(s, 3F, $CF_2CF_3$), 43.57(s, 2F, $CF_2$) |
| 31 | <r.t. | Found: C, 23.58; H, 1.59; N, 6.12<br>Calcd: C, 23.59; H, 1.54; N, 6.11 | 91.22(t, J=8.2Hz, 3F, $CF_3$), 84.32(s, 6F, $SCF_3$) |
| 32 | <r.t. | Found: C, 25.45; H, 1.94; N, 5.97<br>Calcd: C, 25.43; H, 1.92; N, 5.93 | 92.73(t, J=8.5Hz, 3F, $CF_3$), 84.30(s, 6F, $SCF_3$) |
| 33 | <r.t. | Found: C, 28.54; H, 1.50; N, 6.66<br>Calcd: C, 28.45; H, 1.67; N, 6.63 | 91.19(t, J=7.7Hz, 3F, $CF_3$), 87.93(s, 3F, $COCF_3$), 84.56(s, 3F, $SCF_3$) |
| 34 | <r.t. | Found: C, 28.00; H, 1.53; N, 6.02<br>Calcd: C, 27.98; H, 1.49; N, 5.93 | 91.21(t, J=7.7Hz, 3F, $CF_3$), 84.53(s, 3F, $SCF_3$), 81.31(s, 3F, $CF_2$), 43.56(s, 2F, $CF_2CF_3$) |
| 35 | 83.5-85.0 | Found: C, 25.89; H, 3.66; N, 6.13<br>Calcd: C, 25.86; H, 3.69; N, 6.03 | 101.79(t, J=8.4Hz, 3F, $CF_3$), 84.30(s, 6F, $SCF_3$) |
| 36 | 64.0-66.7 | Found: C, 29.01; H, 3.56; N, 5.80<br>Calcd: C, 29.27; H, 4.30; N, 5.69 | 101.81(t, J=8.7Hz, 3F, $CF_3$), 84.23(s, 6F, $SCF_3$) |
| 37 | <r.t. | Found: C, 25.84; H, 3.67; N, 6.08 | 101.38(t, J=8.9Hz, 3F, $CF_3$), 84.29(s, 6F, $SCF_3$) |
| 38 | | Calcd: C, 25.86; H, 3.69; N, 6.03 | |
| 39 | <r.t. | Found: C, 31.40; H, 5.01; N, 5.68<br>Calcd: C, 32.31; H, 4.845; N, 5.38 | 101.80(t, J=9.0Hz, 3F, $CF_3$), 84.31(s, 6F, $SCF_3$) |
| 40 | 65.1-66.4 | Found: C, 26.06; H, 3.38; N, 6.11<br>Calcd: C, 25.98; H, 3.27; N, 6.06 | 102.20(t, J=8.7Hz, 3F, $CF_3$), 84.30(s, 6F, $SCF_3$) |
| 41 | 31.1(DSC)* | Calcd: C, 25.11; H, 3.16; N, 5.86<br>Found: C, 24.97; H, 3.17; N, 5.74 | 102.36(t, J=8.4Hz, 3F, $CF_3$), 84.43(s, 6F, $SCF_3$) |
| 42 | <r.t. | Found: C, 27.93; H, 3.67; N, 5.08<br>Calcd: C, 27.86; H, 3.60; N, 5.00 | 102.29(t, J=7.9Hz, 3F, $CF_3$), 84.30(s, 6F, $SCF_3$) |
| 43 | 80.8-81.9 | Found: C, 25.71; H, 2.94; N, 5.34<br>Calcd: C, 24.82; H, 3.03; N, 5.26 | 102.31(t, J=7.6Hz, 3F, $CF_3$), 84.23(s, 6F, $SCF_3$) |
| 44 | <r.t. | Found: C, 30.90; H, 4.01; N, 6.54<br>Calcd: C, 30.85; H, 4.00; N, 6.54 | 101.39(t, J=8.0Hz, 3F, $CF_3$), 87.92(s, 3F, $COCF_3$), 84.58(s, 3F, $SCF_3$) |
| 45 | <r.t. | Found: C, 30.11; H, 3.65; N, 5.91<br>Calcd: C, 30.13; H, 3.58; N, 5.86 | 101.38(t, J=8.9Hz, 3F, $CF_3$), 84.56(s, 3F, $SCF_3$), 81.32(s, 3F, $CF_2CF_3$), 43.57(s, 2F, $CF_2$) |
| 46 | <r.t. | Found: C, 32.28; H, 3.57; N, 5.24<br>Calcd: C, 32.07; H, 3.84; N, 5.34 | 102.28(t, J=8.2Hz, 6F, $CF_3$), 87.88(s, 3F, $COCF_3$), 84.53(s, 3F, $SCF_3$) |
| 47 | <r.t. | Found: C, 31.50; H, 3.51; N, 4.92<br>Calcd: C, 31.37; H, 3.51; N, 4.88 | 102.28(t, J=7.8Hz, 6F, $CF_3$), 84.52(s, 3F, $SCF_3$), 81.30(s, 3F, $CF_2$), 43.53(s, 2F, $CF_2CF_3$) |
| 48 | 63.7-65.0 | Found: C, 27.76; H, 3.66; N, 4.75<br>Calcd: C, 28.48; H, 3.76; N, 4.74 | 103.53(t, J=8.2Hz, 6F, $CF_3$), 84.27(s, 6F, $SCF_3$) |
| 49 | 55.1-58.0 | Found: C, 24.08; H, 3.06; N, 5.10<br>Calcd: C, 24.09; H, 2.94; N, 5.11 | 103.00(t, J=8.4Hz, 6F, $CF_3$), 84.27(s, 6F, $SCF_3$) |
| 50 | <r.t. | Found: C, 28.30; H, 4.19; N, 5.47<br>Calcd: C, 28.35; H, 4.16; N, 5.51 | 102.43(t, J=9.2Hz, 3F, $CF_3$), 84.28(s, 6F, $SCF_3$) |
| 51 | <r.t. | Found: C, 29.56; H, 3.48; N, 5.28<br>Calcd: C, 29.55; H, 3.24; N, 5.30 | 101.39(t, J=8.6Hz, 3F, $CF_3$), 84.57(s, 3F, $SCF_3$), 82.85(t, J=8.6Hz, 3F, $CF_2CF_3$), 46.96(q, J=9.2Hz, 2F, —$COCF_2$), 37.10(s, 2F, $CF_2CF_3$) |
| 52 | <r.t. | Found: C, 26.84; H, 3.87; N, 5.63<br>Calcd: C, 26.72; H, 3.87; N, 5.67 | 102.42(t, J=8.1Hz, 3F, $CF_3$), 84.30(s, 6F, $SCF_3$) |
| 53 | <r.t. | Found: C, 32.00; H, 4.16; N, 5.43<br>Calcd: C, 32.19; H, 4.05; N, 5.36 | 102.43(t, J=8.9Hz, 3F, $CF_3$), 84.55(s, 3F, $SCF_3$), 81.32(s, 3F, $CF_2CF_3$), 43.59(s, 2F, $COCF_2$) |
| 54 | <r.t. | Found: C, 25.02; H, 3.69; N, 5.81<br>Calcd: C, 25.00; H, 3.57; N, 5.83 | 101.76(t, J=8.7Hz, 3F, $CF_3$), 84.32(s, 6F, $SCF_3$) |

TABLE 8-continued

Properties, elemental analyses, and spectral data of the products.

| Ex. | m.p. | Elemental Analysis | $^{19}$F-NMR (in acetonitrile-$d_3$; standard $C_6F_6$) |
|---|---|---|---|
| 55 | <r.t. | Found: C, 23.15; H, 3.27; N, 6.02<br>Calcd: C, 23.18; H, 3.24; N, 6.01 | 101.75(t, J=8.9Hz, 3F, $CF_3$), 84.32(s, 6F, $SCF_3$) |
| 56 | <r.t. | Found: C, 25.53; H, 3.26; N, 5.06<br>Calcd: C, 25.63; H, 3.23; N, 4.98 | 102.37(t, J=8.5Hz, 3F, $CF_3$), 89.38(t, J=8.8Hz, 3F, —$OCH_2CF_3$), 84.32(s, 6F, $SCF_3$) |
| 57 | <r.t. | Found: C, 27.52; H, 3.19; N, 5.87<br>Calcd: C, 27.51; H, 3.15; N, 5.83 | 101.74(t, J=9.0Hz, 3F, $CF_3$), 84.55(s, 3F, $SCF_3$), 81.32(s, 3F, $CF_2CF_3$), 43.59(s, 2F, $COCF_2$) |
| 58 | <r.t. | Found: C, 29.16; H, 3.45; N, 5.68<br>Calcd: C, 29.16; H, 3.47; N, 5.67 | 101.75(t, J=8.2Hz, 3F, $CF_3$), 84.56(s, 3F, $SCF_3$), 81.33(s, 3F, $CF_2CF_3$), 43.59(s, 2F, $COCF_2$) |
| 59 | <r.t. | Found: C, 26.64; H, 3.84; N, 5.73<br>Calcd: C, 26.72; H, 3.87; N, 5.67 | 100.77(t, J=8.3Hz, 3F, $CF_3$), 83.63(s, 6F, $SCF_3$) |
| 60 | <r.t. | Found: C, 25.87; H, 3.76; N, 5.56<br>Calcd: C, 25.89; H, 3.75; N, 5.49 | 101.73(t, J=8.1Hz, 3F, $CF_3$), 84.28(s, 6F, $SCF_3$) |
| 61 | <r.t. | Found: C, 29.45; H, 3.60; N, 5.27<br>Calcd: C, 29.78; H, 3.65; N, 5.34 | 101.72(t, J=8.5Hz, 3F, $CF_3$), 84.53(s, 3F, $SCF_3$), 81.31(s, 3F, $CF_2CF_3$), 43.57(s, 2F, $COCF_2$) |
| 62 | <r.t. | Found: C, 19.34; H, 2.54; N, 6.64<br>Calcd: C, 19.18; H, 2.53; N, 6.39 | 100.10(t, 2.17F, J=8.6Hz, impurity), 90.62(t, J=7.9Hz, 3F, $CF_3$), 83.64(s, 11.72F, $SCF_3$) |
| 63 | 67.4-69.1 | Found: C, 24.99; H, 3.24; N, 5.98<br>Calcd: C, 25.00; H, 3.57; N, 5.83 | 101.78(t, 0.27F, J=8.5Hz, impurity), 91.94(t, 3F, J=8.4Hz, $CF_3$), 84.28(s, 6.81F, $SCF_3$) |
| 64 | <r.t. | Found: C, 24.97; H, 3.61; N, 6.20<br>Calcd: C, 25.00; H, 3.57; N, 5.83 | 101.38(t, J=9.1Hz, 1.32F, impurity), 91.47(t, J=7.8Hz, 3F, $CF_3$), 84.30(s, 11.51F, $SCF_3$) |
| 65 | <r.t. | Found: C, 21.21; H, 2.69; N, 3.13<br>Calcd: C, 21.19; H, 2.67; N, 3.09 | 101.88(t, J=9.0Hz, $CF_3$), 84.25(s, $SCF_3$) |
| 66 | 59.0-60.2 | Found: C, 21.39; H, 2.50; N, 2.87<br>Calcd: C, 21.47; H, 2.40; N, 2.78 | 84.24(s, $SCF_3$), 79.44(s, $CF_2CF_3$), 51.78(t, J=16.7Hz, $CF_2$) |
| 67 | 31.9(DSC)* | Found: C, 19.18; H, 2.28; N, 3.21<br>Calcd: C, 19.14; H, 2.29; N, 3.19 | 102.06(t, J=8.8Hz, 3F, $CF_3$), 84.31(s, 6F, $SCF_3$) |
| 68 | <r.t. | Found: C, 34.00; H, 5.03; N, 2.51<br>Calcd: C, 33.98; H, 4.99; N, 2.48 | 101.88(t, J=9.4Hz, 3F, $CF_3$), 84.33(s, 6F, $SCF_3$) |
| 69 | 52.1-53.5 | Found: C, 19.10; H, 1.78; N, 2.81<br>Calcd: C, 18.94; H, 1.79; N, 2.76 | 102.21(t, J=8.6Hz, 3F, $CF_3$), 84.28(s, 6F, $SCF_3$) |
| 70 | 60.2-62.4 | Found: C, 24.95; H, 2.79; N, 2.55<br>Calcd: C, 25.58; H, 3.04; N, 2.49 | 102.16(t, J=8.5Hz, 3F, $CF_3$), 84.29(s, 6F, $SCF_3$) |
| 71 | <r.t. | Found: C, 25.90; H, 2.92; N, 3.28<br>Calcd: C, 25.90; H, 2.90; N, 3.36 | 101.90(t, J=9.5Hz, 3F, $CF_3$), 87.92(s, 3F, $COCF_3$), 84.57(s, 3F, $SCF_3$) |
| 72 | <r.t. | Found: C, 25.79; H, 2.59; N, 3.02<br>Calcd: C, 25.70; H, 2.59; N, 3.00 | 101.88(t, J=9.4Hz, 3F, $CF_3$), 84.55(s, 3F, $SCF_3$), 81.32(s, 3F, $CF_2CF_3$), 43.57(s, 2F, $CF_2$) |
| 73 | 48.5-49.7 | Found: C, 19.48; H, 1.26; N, 6.61<br>Calcd: C, 19.45; H, 1.17; N, 6.48 | 93.43(t, J=8.1Hz, 3F, $CF_3$), 84.31(s, 6F, $SCF_3$) |
| 74 | 41.6-44.1 | Found: C, 18.69; H, 1.16; N, 6.29<br>Calcd: C, 18.75; H, 1.12; N, 6.25 | 92.87(t, J=8.0Hz, 3F, $CF_3$), 84.34(s, 6F, $SCF_3$) |
| 75 | <r.t. | Found: C, 19.48; H, 1.42; N, 6.49<br>Calcd: C, 19.45; H, 1.17; N, 6.48 | 93.91(t, J=8.0Hz, 3F, $CF_3$), 84.34(s, 6F, $SCF_3$) | r.t.: room temperature (about 25° C.)
DSC: differential scanning calorimetry
*Melting point is determined by DSC.

EXAMPLE 76

Measurement of Oxidation Potential and Reduction Potential by Cyclic Voltammetry Cyclic voltammogram for the following compounds were measured, and the potential window of each compound was determined. As a comparative example, EMI-TFSI (1-ethyl-3-methylimidazolium bis(trifluoromethanesulfonyl)imide) was used.

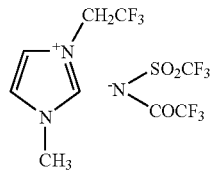
I-1 (Ex. 12)

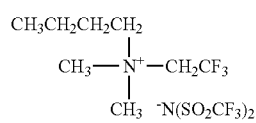
A-1 (Ex. 37 or 38)

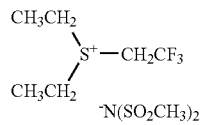
S-1 (Ex. 65)

-continued

Comparative Example: EMI-TFSI

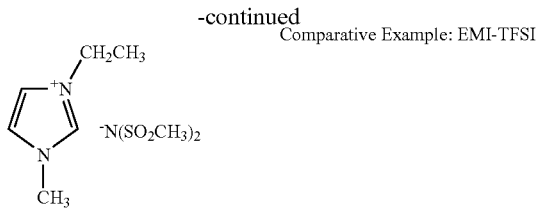

Conditions for cyclic voltammetry are as follows:
Working electrode: Pt electrode
Electrode couple-reference electrode: Ag
Voltage scan rate: 50 mV/sec The oxidation potential and the reduction potential of each compound that were measured by cyclic voltammetry are shown in the table below.

TABLE 9

|  | I-1 | A-1 | S-1 | Comparative Example EMI-TFSI |
| --- | --- | --- | --- | --- |
| Oxidation potential (V vs Li) | 5.8 | 5.8 | 5.9 | 5.9 |
| Reduction potential (V vs Li) | 1.4 | 0.5 | 1.2 | 1.5 |
| Difference between oxidation potential and reduction potential | 4.4 | 5.3 | 4.7 | 4.4 |

As shown in Table 9, the compound of the present invention has a potential window (a difference between the oxidation potential and the reduction potential) equivalent to or wider than that of conventional ambient-temperature molten salts.

EXAMPLE 77

Ion Conductivity

Ion conductivities of the following compounds I-1 (compound of Ex. 12) and TFEMI-TFSI (comparative compound) were measured. The results are shown in FIG. 1.

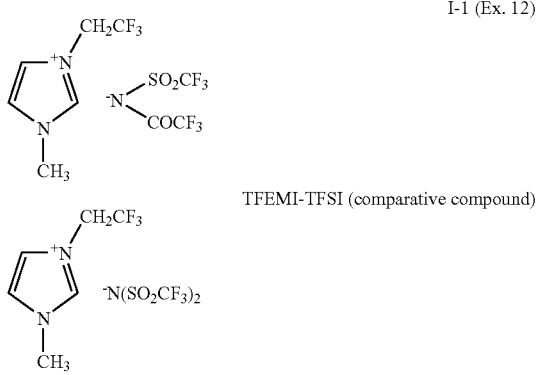

As is apparent from FIG. 1, ion conductivity of ambient-temperature molten salt I-1 is enhanced in a high temperature region compared with TFEMI-TFSI.

All publications cited herein are incorporated herein by reference in their entirety.

INDUSTRIAL APPLICABILITY

According to the present invention, with the use of the compound of formula (VII) or (IX), fluoroalkyl and imide anion can be simultaneously introduced to a heteroatom-containing compound such as imidazole, thereby easily obtaining ambient-temperature molten salts. Since the ambient-temperature molten salts of the present invention have wide potential windows, excellent stability and high ion conductivities, they are useful for electrolytes for lithium cells or the like.

What is claimed is:

1. Ambient-temperature molten salts of formula (I):

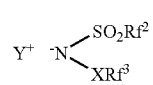

wherein
$Y^+$ is a sulfonium ion of formula (III):

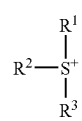

wherein $R^1$ to $R^3$ are independently hydrogen atoms, $C_{1-10}$ alkyl, $C_{1-10}$ alkyl having ether linkage, or —$CH_2Rf^1$, wherein $Rf^1$ is $C_{1-10}$ perfluoroalkyl, provided that at least one of $R^1$ to $R^3$ is —$CH_2Rf^1$;
$Rf^2$ and $Rf^3$ are independently $C_{1-10}$ perfluoroalkyl or may together form $C_{1-4}$ perfluoroalkylene; and,
X is —$SO_2$— or —CO—.

2. The ambient-temperature molten salts according to claim 1,
wherein $R^1$ to $R^3$ are independently hydrogen atoms, $C_{1-6}$ alkyl or —$CH_2Rf^1$, wherein $Rf^1$ is $C_{1-4}$ perfluoroalkyl, provided that at least one of $R^1$ to $R^3$ is —$CH_2Rf^1$.

3. A fluoroalkylfluorophenyliodonium imide compound of formula (VII):

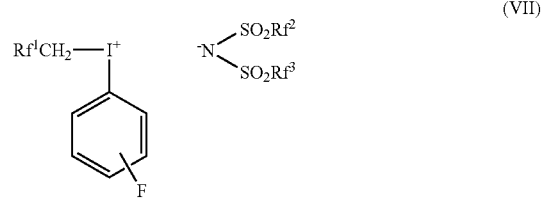

wherein $Rf^1$ is $C_{1-10}$ perfluoroalkyl, $Rf^2$ and $Rf^3$ are independently $C_{1-10}$ perfluoroalkyl or together form $C_{1-4}$ perfluoroalkylene.

4. A method for producing a compound of formula (I):

wherein
Y$^+$ is sulfonium ion of formula (III):

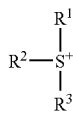
(III)

wherein R$^1$ to R$^3$ are independently hydrogen atoms, C$_{1-10}$ alkyl, C$_{1-10}$ alkyl having ether linkage, or —CH$_2$Rf$^1$, wherein Rf$^1$ is C$_{1-10}$ perfluoroalkyl, provided that at least one of R$^1$ to R$^3$ is —CH$_2$Rf$^1$;
Rf$^2$ and Rf$^3$ are independently C$_{1-10}$ perfluoroalkyl or may together form C$_{1-4}$ perfluoroalkylene, and
X is —SO$_2$—,
which comprises reacting a sulfide, which may be optionally substituted with C$_{1-10}$ alkyl, C$_{1-10}$ alkyl having ether linkage, or —CH$_2$Rf$^1$, wherein Rf$^1$ is C$_{1-10}$ perfluoroalkyl, with a compound of formula (IX):

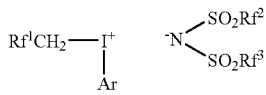
(IX)

wherein Rf$^1$, Rf$^2$, and Rf$^3$ are as defined above, and —Ar is an unsubstituted phenyl or phenyl that may be optionally substituted with halogen atom or C$_{1-10}$ alkyl, to give a compound of formula (I).

5. The method according to claim 4, wherein —Ar is phenyl or represented by the following formula:

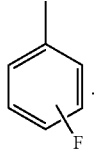

6. The method according to 4, wherein —Ar is represented by the following formula:

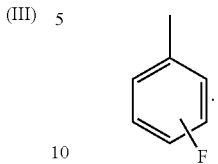

7. The ambient-temperature molten salts according to claim 1, wherein Rf$^1$ is C$_{1-7}$ perfluoroalkyl.

8. The ambient-temperature molten salts according to claim 7, wherein Rf$^1$ is C$_{1-4}$ perfluoroalkyl.

9. The ambient-temperature molten salts according to claim 1, wherein X is —SO$_2$—.

10. The ambient-temperature molten salts according to claim 1, wherein X is —CO—.

11. Ambient-temperature molten salts chosen from

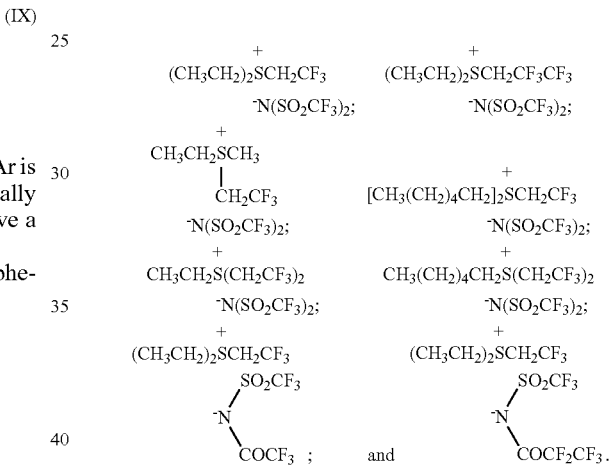

UNITED STATES PATENT AND TRADEMARK OFFICE
CERTIFICATE OF CORRECTION

PATENT NO. : 7,534,509 B2  
APPLICATION NO. : 10/979220  
DATED : May 19, 2009  
INVENTOR(S) : Teruo Umemoto Page 1 of 1

It is certified that error appears in the above-identified patent and that said Letters Patent is hereby corrected as shown below:

Claim 1, col. 48, line 31, "atoms" should read --atom--.

Claim 2, col. 48, line 41, "atoms" should read --atom--.

Claim 4, col. 49, line 2, "is sulfonium" should read --is a sulfonium--.

Claim 4, col. 49, line 11, "atoms" should read --atom--.

Claim 6, col. 50, line 1, "to 4" should read --to claim 4--.

Signed and Sealed this

Seventeenth Day of November, 2009

David J. Kappos  
*Director of the United States Patent and Trademark Office*